(12) United States Patent
Mistretta et al.

(10) Patent No.: US 10,137,145 B2
(45) Date of Patent: Nov. 27, 2018

(54) **MENINGOCOCCAL VACCINE BASED ON LIPOOLIGOSACCHARIDE (LOS) ORIGINATING FROM MODIFIED *NEISSERIA MENINGITIDIS* STRAINS OF IMMUNOTYPE L6**

(71) Applicants: Noelle Mistretta, Sain Bel (FR); Monique Moreau, Lyons (FR); Genevieve Renauld-Mongenie, Chaponost (FR); Bachra Rokbi, Lyons (FR)

(72) Inventors: Noelle Mistretta, Sain Bel (FR); Monique Moreau, Lyons (FR); Genevieve Renauld-Mongenie, Chaponost (FR); Bachra Rokbi, Lyons (FR)

(73) Assignee: Sanofi Pasteur SA, Lyons (FR)

( * ) Notice: Subject to any disclaimer, the term of this patent is extended or adjusted under 35 U.S.C. 154(b) by 0 days.

(21) Appl. No.: 15/584,619

(22) Filed: May 2, 2017

(65) Prior Publication Data
US 2018/0036339 A1 Feb. 8, 2018

Related U.S. Application Data

(60) Continuation of application No. 14/756,143, filed on Aug. 5, 2015, now Pat. No. 9,669,052, which is a division of application No. 12/800,454, filed on May 14, 2010, now Pat. No. 9,132,181.

(60) Provisional application No. 61/271,986, filed on Jul. 29, 2009.

(30) Foreign Application Priority Data

May 14, 2009 (FR) ..................... 09 02333

(51) Int. Cl.
*A61K 39/095* (2006.01)
*A61K 31/739* (2006.01)
*A61K 9/127* (2006.01)

(52) U.S. Cl.
CPC ............ *A61K 31/739* (2013.01); *A61K 9/127* (2013.01); *A61K 39/095* (2013.01)

(58) Field of Classification Search
CPC .... A61K 39/095; A61K 31/739; A61K 9/127; A61K 2039/55566; A61K 2039/6037; A61K 39/102; A61K 39/1045; A61K 2039/60; A61K 2039/70; C08B 37/0063; C07K 14/22; C07K 2319/00
See application file for complete search history.

(56) References Cited

U.S. PATENT DOCUMENTS 9,132,181 B2 * 9/2015 Mistretta .............. A61K 39/095
9,669,052 B2 * 6/2017 Mistretta .............. A61K 39/095

FOREIGN PATENT DOCUMENTS

EP 1748791 B1 2/2007

* cited by examiner

*Primary Examiner* — Sarvamangala Devi
(74) *Attorney, Agent, or Firm* — McDonnell Boehnen Hulbert & Berghoff LLP

(57) ABSTRACT

The invention especially relates to multivalent vaccine compositions that can treat or prevent at least 60, preferably 75% of infections caused by *Neisseria meningitidis* especially of serogroup B. To this end, the invention in particular provides a lipooligosaccharide (LOS) of *N. meningitidis* in particular constituted by a lipid A, an inner core, an α chain of L6 or L8 type, in which the heptose II residue of the inner core bears in position O-3 and in position O-6 or O-7 a phosphoethanolamine (PEA) substituent, and also to the construction of the strain of *N. meningitidis* that is capable of expressing such an LOS. The invention also relates to a strain of *N. meningitidis* of serogroup A that bears a lipooligosaccharide (LOS) in particular constituted by a lipid A, an inner core, an α chain of L6 type, in which the heptose II residue of the inner core bears in position O-3 a phosphoethanolamine (PEA) substituent and does not bear a PEA substituent in positions O-6 and O-7. The LOSs cited or originating from the mentioned strains may be used as vaccine antigens, especially in multivalent, e.g. divalent compositions, so as to offer protection against the major epidemiological complexes of *N. meningitidis*, especially of serogroup B.

12 Claims, 3 Drawing Sheets
(2 of 3 Drawing Sheet(s) Filed in Color)
Specification includes a Sequence Listing.

SEQUENCE LISTING

```
<160> NUMBER OF SEQ ID NOS: 24

<210> SEQ ID NO 1
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is a peptide of 2 to 5 and preferably 3 or
      4 amino acid residues, in which at least 2 amino acid residues are
      independently chosen from Lys, Hyl (hydroxylysine), Arg and His.
<220> FEATURE:
<221> NAME/KEY: MISC_FEATURE
<222> LOCATION: (3)..(3)
<223> OTHER INFORMATION: Xaa is a peptide of 3 to 7 and preferably 4 or
      5 amino acid residues, which comprises at least two and preferably
      three amino acid residues chosen from Val, Leu, Ile, Phe, Tyr and
      Trp.
<220> FEATURE:
<221> NAME/KEY: MISC_FEATURE
```

```
<222> LOCATION: (5)..(5)
<223> OTHER INFORMATION: Xaa is optional (this position may or may not
      be empty) and is an amino acid residue or a peptide formed from 2
      to 3 amino acid residues.

<400> SEQUENCE: 1

Xaa Cys Xaa Cys Xaa
1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic

<400> SEQUENCE: 2

Lys Thr Lys Cys Lys Phe Leu Lys Lys Cys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic

<400> SEQUENCE: 3

Lys Thr Lys Cys Lys Phe Leu Leu Leu Cys
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is hydroxylysine

<400> SEQUENCE: 4

Lys Arg His Xaa Cys Lys Arg Ile Val Leu Cys
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic

<400> SEQUENCE: 5

Lys Arg His Cys Val Leu Ile Trp Tyr Phe Cys
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic

<400> SEQUENCE: 6

Lys Thr Lys Cys Lys Phe Leu Leu Leu Cys
1               5                   10
```

```
<210> SEQ ID NO 7
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is hydroxylysine

<400> SEQUENCE: 7

Xaa Arg His Lys Cys Phe Tyr Trp Val Ile Leu Cys
 1               5                  10

<210> SEQ ID NO 8
<211> LENGTH: 42
<212> TYPE: DNA
<213> ORGANISM: Artificial Sequence
<220> FEATURE:
<223> OTHER INFORMATION: Synthetic

<400> SEQUENCE: 8
cggaattcgc cgtctcaaat gaaaaaatcc cttttcgttc tc                    42

<210> SEQ ID NO 9
<211> LENGTH: 31
<212> TYPE: DNA
<213> ORGANISM: Artificial Sequence
<220> FEATURE:
<223> OTHER INFORMATION: Synthetic

<400> SEQUENCE: 9
aactgcagtc attgcggata aacatattcc g                                31

<210> SEQ ID NO 10
<211> LENGTH: 23
<212> TYPE: DNA
<213> ORGANISM: Artificial Sequence
<220> FEATURE:
<223> OTHER INFORMATION: Synthetic

<400> SEQUENCE: 10
cgccgaatac tttatcttga ggc                                         23

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
ctcgccaaag agcagggc                                               18

<210> SEQ ID NO 12
<211> LENGTH: 43
<212> TYPE: DNA
<213> ORGANISM: Artificial Sequence
<220> FEATURE:
<223> OTHER INFORMATION: Synthetic

<400> SEQUENCE: 12
cggaattcgc cgtctcaagg ttgcctatgt tttcctgttt ttg                   43

<210> SEQ ID NO 13
```

<211> LENGTH: 32
<212> TYPE: DNA
<213> ORGANISM: Artificial Sequence
<220> FEATURE:
<223> OTHER INFORMATION: Synthetic

<400> SEQUENCE: 13
aactgcagct aacgggcaat tttcaaaacg tc                                    32

<210> SEQ ID NO 14
<211> LENGTH: 26
<212> TYPE: DNA
<213> ORGANISM: Artificial Sequence
<220> FEATURE:
<223> OTHER INFORMATION: Synthetic

<400> SEQUENCE: 14
cgggatccca tcgacacgaa cgccgc                                           26

<210> SEQ ID NO 15
<211> LENGTH: 28
<212> TYPE: DNA
<213> ORGANISM: Artificial Sequence
<220> FEATURE:
<223> OTHER INFORMATION: Synthetic

<400> SEQUENCE: 15
cgggatcccc gcgcttaacg actacatc                                         28

<210> SEQ ID NO 16
<211> LENGTH: 25
<212> TYPE: DNA
<213> ORGANISM: Artificial Sequence
<220> FEATURE:
<223> OTHER INFORMATION: Synthetic

<400> SEQUENCE: 16
gtcgatggga tccccgcgct taacg                                            25

<210> SEQ ID NO 17
<211> LENGTH: 18
<212> TYPE: DNA
<213> ORGANISM: Artificial Sequence
<220> FEATURE:
<223> OTHER INFORMATION: Synthetic

<400> SEQUENCE: 17
ccgactggcg gaattggg                                                    18

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
cccatttctt cctgacggac                                                  20

<210> SEQ ID NO 19
<211> LENGTH: 38
<212> TYPE: DNA
<213> ORGANISM: Artificial Sequence
<220> FEATURE:
<223> OTHER INFORMATION: Synthetic

<400> SEQUENCE: 19

```
cggaattcgc cgtctcaaat gccgtctgaa gccttcag                              38

<210> SEQ ID NO 20
<211> LENGTH: 29
<212> TYPE: DNA
<213> ORGANISM: Artificial Sequence
<220> FEATURE:
<223> OTHER INFORMATION: Synthetic

<400> SEQUENCE: 20
aactgcagaa cggtttttca gcaatcggt                                        29

<210> SEQ ID NO 21
<211> LENGTH: 29
<212> TYPE: DNA
<213> ORGANISM: Artificial Sequence
<220> FEATURE:
<223> OTHER INFORMATION: Synthetic

<400> SEQUENCE: 21
cgggatccgg aaggcccgag cgcagaagt                                        29

<210> SEQ ID NO 22
<211> LENGTH: 32
<212> TYPE: DNA
<213> ORGANISM: Artificial Sequence
<220> FEATURE:
<223> OTHER INFORMATION: Synthetic

<400> SEQUENCE: 22
gctctagaca acttacttct gacaacgatc gg                                    32

<210> SEQ ID NO 23
<211> LENGTH: 29
<212> TYPE: DNA
<213> ORGANISM: Artificial Sequence
<220> FEATURE:
<223> OTHER INFORMATION: Synthetic

<400> SEQUENCE: 23
cgggatccgc caattcatcc agcccgatg                                        29

<210> SEQ ID NO 24
<211> LENGTH: 26
<212> TYPE: DNA
<213> ORGANISM: Artificial Sequence
<220> FEATURE:
<223> OTHER INFORMATION: Synthetic

<400> SEQUENCE: 24
cgtctagacc cggttcgaca gccttg                                           26
```

MENINGOCOCCAL VACCINE BASED ON LIPOOLIGOSACCHARIDE (LOS) ORIGINATING FROM MODIFIED *NEISSERIA MENINGITIDIS* STRAINS OF IMMUNOTYPE L6

This application is a continuation of U.S. application Ser. No. 14/756,143, filed on Aug. 5, 2015, which is a divisional of U.S. application Ser. No. 12/800,454, filed on May 14, 2010, now U.S. Pat. No. 9,132,181, which claims priority to U.S. Provisional Patent Application Ser. No. 61/271,986 filed on Jul. 29, 2009, the contents of each of which are incorporated herein by reference in their entirety.

The invention relates to the field of vaccines for combating infections caused by *Neisseria meningitidis* and especially proposes a vaccine composition comprising two types of lipooligosaccharide (LOS), each of the two types originating from a particular strain of *N. meningitidis*. The invention also proposes intermediate means contributing toward the preparation of the vaccine composition mentioned above.

In the field of vaccines, one of the major challenges in the near future will especially be the marketing of a vaccine intended for preventing all the infections caused by *N. meningitidis* serogroup B. This bacterium is responsible for a certain number of pathologies, the dominant ones of which are meningitis and meningococcia, but also arthritis and pericarditis. Meningococcia may be complicated with purpura fulminans and fatal septic shock.

In general, meningitis is either of viral origin or of bacterial origin. In developed countries, the bacteria mainly responsible are: *N. meningitidis* and *Streptococcus pneumoniae*, which are involved, respectively, in about 40% and 50% of the cases of bacterial meningitis. In developing countries, *Haemophilus influenzae* also remains a significant source of meningitis.

In France, about 600 to 800 cases of *N. meningitides*-mediated meningitis are reported per year. In the United States, the number of cases rises to about 2500 to 3000 per year.

The species *N. meningitidis* is subdivided into serogroups according to the nature of the capsule polysaccharides. Although there are about a dozen serogroups, 90% of the cases of meningitis are attributable to the serogroups: A, B, C, Y and W135.

Efficient vaccines based on capsule polysaccharides exist for preventing the *N. meningitidis*-mediated meningitis of the serogroups A, C, Y and W135. These polysaccharides per se are not or are only sparingly immunogenic in children under 2 years old and do not induce any immune memory. However, these drawbacks may be overcome by combining these polysaccharides with a carrier protein.

However, the capsule polysaccharide of *N. meningitidis* serogroup B is not or only sparingly immunogenic in man, whether or not it is in conjugated form (Bruge et al, Vaccine (2004) 22: 1087). Moreover, this polysaccharide bears an epitope that might potentially undergo a cross reaction with human tissues. Thus, it appears highly desirable to search for a vaccine for combating meningitis induced by *N. meningitidis* especially of the serogroup B other than a vaccine based on capsule polysaccharide.

The liposaccharide (LPS) is a major constituent of the outer membrane of the wall of Gram-negative bacteria. LPS is toxic at high doses to mammals and, in view of this biological activity, has been called an endotoxin. It is responsible for septic shock, a fatal pathology which develops following acute infection with a Gram-negative bacterium.

Nevertheless, LPS is not only toxic, it is also immunogenic. In mammals, anti-LPS antibodies are generated during carrying and infection and can be protective. Thus, the use of LPS has already been envisioned in the prophylaxis of infections due to Gram-negative bacteria and associated diseases.

The structure of LPS is in particular constituted of a lipid portion, called lipid A, covalently bonded to a polysaccharide portion.

Lipid A is responsible for the toxicity of LPS. It is highly hydrophobic and enables the LPS to be anchored in the outer membrane of the wall. Lipid A is composed of a disaccharide structure substituted with fatty acid chains. The number and the composition of the fatty acid chains vary from one species to the other.

The polysaccharide portion is in particular constituted of carbohydrate chains which are responsible for the antigenicity. At least 3 major regions can be distinguished in this polysaccharide portion:

(i) an inner core in particular constituted of monosaccharides [one or more KDO (2-keto-3-deoxyoctulosonic acid) and one or more heptoses (Hep)] which are invariant within the same bacterial species;

(ii) an outer core bonded to heptose and in particular constituted of various monosaccharides; and (iii) an O-specific outer chain in particular constituted of a series of repeating units—these repeating units themselves being composed of one or more different monosaccharides.

The structure of LPS varies from one species to another. This is why, for example, in a certain number of non-enteric Gram-negative bacteria such as Neisseriae, Bordetellae, Branhamellas, *Haemophilus* and Moraxellae, the O-specific chain does not exist. The LPS saccharide portion of these bacteria is in particular constituted only of the oligosaccharide core. Consequently, the LPS from these bacteria is often called lipooligosaccharide (LOS).

The structure of the LPS varies not only from one species to another, but also within the same species.

Thus, not all the strains of *N. meningitidis* have an LOS of the same structure, although all the LOSs of meningococcus share the basic structure, which is represented schematically in the following structural formula:

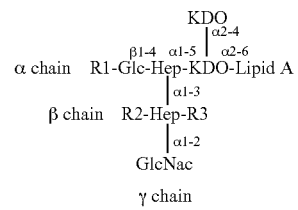

The outer core (or α chain) is variable as a function of the type of oligosaccharide (substituent R1) attached to the glucose residue borne by the heptose I.

Whereas lipid A is essentially invariable, the inner core, which itself also is formed in an invariant manner from two KDO (2-keto-3-deoxyoctulosonic acid) and two heptoses (HepI and HepII), bears various substituents (i) on heptose II (substituents R2 and R3); and (ii) on the γ chain, formed from an N-acetyl glucosamine (GlcNAc), which may or may not be O-acetylated. In the literature, the R2 residue is commonly referred to as the β chain, when R2 is a glucose residue.

Originally, the LOS from N. meningitidis was listed as 13 immunotypes (IT L1 to L13), as a function of its reactivity with a series of antibodies (Achtman et al, 1992, J. Infect. Dis. 165: 53-68). The majority of invasive strains with N. meningitidis serogroup B is of immunotype L3,7 as demonstrated by the reactivity of these strains with a monoclonal antibody called L3,7,9. This monoclonal antibody is capable of recognizing each of the immunotypes L3, L7 and L9 (Gu et al, J. Clin. Microbiol. (1992) 30: 2047; Moran et al, Infect. Immun. (1994) 62 (12): 5290; et Scholten et al, J. Med. Microbiol. (1994) 41: 236). The differences between immunotypes originate from variations in the composition and in the conformation of the oligosaccharide chains. This shows in the table below (Table I), derived from Table 2 of Braun et al, Vaccine (2004) 22: 898, supplemented with data obtained subsequently and relating to immunotypes L9 (Schoudhury et al, Carbohydr. Res. (2008) 343: 2771) and L11 (Mistretta et al, (2008) Poster at the 16th International Pathogenic Neisseria Conference, Rotterdam):

TABLE I

| IT | R1 (α chain) | R2 | R3 |
|---|---|---|---|
| L1 | NeuNAcα2-6Galα1-4Galβ1-4 | PEA-3 | — |
| L2 | NeuNAcα2-3Galβ1-4GlcNAcβ1-3Galβ1-4 | Glcα (1-3) | PEA-6 or PEA-7 |
| L3 | NeuNAcα2-3Galβ1-4GlcNAcβ1-3Galβ1-4 | PEA-3 | — |
| L4 | NeuNAcα2-3Galβ1-4GlcNAcβ1-3Galβ1-4 | — | PEA-6 |
| L5 | NeuNAcα2-3Galβ1-4GlcNAcβ1-3Galβ1-4Glcβ1-4 | Glcα (1-3) | — |
| L6 | GlcNAcβ1-3Galβ1-4 | — | PEA-6 or PEA-7 |
| L7 | Galβ1-4GlcNAcβ1-3Galβ1-4 | PEA-3 | — |
| L8 | Galβ1-4 | PEA-3 | — |
| L9 | Galβ1-4GlcNAcβ1-3Galβ1-4 | — | PEA-6 |
| L10 | n.d. | n.d. | n.d. |
| L11 | Glcβ1-4 | PEA-3 | PEA-6. |
| L12 | n.d | n.d. | n.d. |
| L13 | n.d | n.d. | n.d. | n.d.: not determined.

It may be noted, inter alia, that certain LOSs may be sialylated (presence of N-acetylneuraminic acid on the terminal galactose residue (Gal) of the α chain). Thus, immunotypes L3 and L7 differ only by the respective presence/absence of this sialylation. Moreover, most LOSs are substituted with an O-acetyl group on the glucosamine residue ((α-GlcNAc) of the inner core (Wakarchuk et al. (1998) Eur. J. Biochem. 254: 626; Gamian et al. (1992) J. Biol. Chem. 267: 922; Kogan et al (1997) Carbohydr. Res. 298: 191; Di Fabio et al. (1990) Can. J. Chem. 68: 1029; Michon et al. (1990) J. Biol. Chem. 275: 9716; Choudhury et al. (above); and Mistretta et al. (above)).

The other variations in the structure of the LOS are due to different genetic factors, including:
(i) the presence/absence of certain genes involved in the LOS biosynthetic pathway and in possible mutual associations of the genes;
(ii) the phase variation to which certain genes are subjected;
(iii) homologous recombination [since certain genes have conserved regions (lgtB, lgtE and lgtH) and other genes are hybrid (lgtZ is the hybrid of the genes lgtA and lgtB), rearrangements may take place]; and
(iv) mutations.

The genes involved in the LOS biosynthetic pathway (with the exception of two) are divided into three loci (lgt-1, lgt-2 and lgt-3). The description of these genes and their function is given later, illustrated schematically by FIG. 1, which shows the structure of the LOS of N. meningitidis, the various sites at which the variability is expressed and also the levels of intervention of the genes.

The off-locus genes are lpt3 and lot3. The gene lpt3 codes for a PEA transferase. This enzyme has the capacity to attach a phosphoethanolamine (PEA) residue in the O-3 position of heptose II. The gene lot3 codes for an LOS O-acetyltransferase that has the capacity to O-acetylate the γ chain. It is subject to a phase variation.

The lgt-1 locus comprises 7 genes: lgtA, lgtB, lgtC, lgtD, lgtE, lgtH and lgtZ, each coding for a particular glycosyl transferase. Among these genes, lgtA and lgtC are subject to a phase variation. lgtE and lgtH have an allelic variation: the codon that determines the amino acid in position 153 codes either for a threonine residue (and in this case the resulting enzyme is a Gal-transferase) or for a methionine residue (and in this case the resulting enzyme is a Glc-transferase).

The lgt-1 locus is classed into 8 genetic types (Zhu et al, Microbiology (2002) 148: 1833).

The lgt-2 locus comprises 2 genes: lgtF and lgtK coding for glycosylases. The product of the lgtF gene intervenes in the construction of the α chain by enabling the binding of the glucose residue to heptose I, and therefore does not intervene in the nature of the immunotype; nor, for that matter, does the gene lgtK.

The lgt-3 locus comprises 2 genes: lgtG and lpt6. The gene lgtG codes for a Glc synthetase that has the capacity to attach a glucose residue in the O-3 position of heptose II. The gene lpt6 codes for a PEA transferase that has the capacity to attach a phosphoethanolamine (PEA) substituent in the O-6 or O-7 position of heptose II. The gene lgtG is subject to a phase variation. When it is "On" and accompanied by a functional lpt3 gene, the attachment of the glucose residue always takes place at the expense of PEA (whose attachment is mediated by lpt3).

The lgt-3 locus is classed into 5 genetic types (Wright et al., J. Bact. (October 2004): 6970).

The Galβ1-4GlcNAcβ1-3Galβ1-4Glcβ1-4 carbohydrate unit or lacto-N-neotetraose unit which is present in the α chain of certain N. meningitidis LOS immunotypes constitutes an epitope which can potentially crossreact with human erythrocytes. Thus, with a view to producing a vaccine for use in humans, it is advisable to choose an LOS which does not possess this unit. It may therefore be particularly advantageous to use an LOS originating from strains of immunotype L6 or L8.

However, a genotype study of epidemiological strains made it possible to discover that the strains of immunotype L6 or L8 needed to be optimized in order to modify the structure of their original LOS; this being in order to manufacture an improved LOS-based vaccine.

The genotype study in question was performed in two stages.

First, about twenty strains of N. meningitidis were analyzed both by genotyping and by biochemical analysis (mass spectrometry and nuclear magnetic resonance). In a first stage, the immunotype of these strains was predicted from the genotyping results. The results of the biochemical analysis revealed an excellent correlation between the structure effectively determined and the immunotype predicted by genotyping. Given the close parallel between the genotyping results and the biochemical analysis results, it was possible in a second stage to validly continue the analysis of a much broader collection of strains, solely by genotyping.

Thus, a collection of 163 strains was gathered, most of which were provided by the laboratories of Drs D.A. Caugant (NIPH, Oslo, Norway), D. Martin (ESR, Porirua, New Zealand) and M. Diggle (SMPRL, Glasgow, United Kingdom). The strains of this collection are sourced worldwide. About half of them were isolated in Europe. They are in the very large majority of serogroup B and are divided into the 6 major epidemiological complexes found in Europe in the invasive strains of the serogroup B: i.e. the MLST (multilocus sequence type) ST-8, ST-11, ST-18, ST 32, ST-41/44 and ST-269 complexes.

Specifically, epidemiologically, the most recent European data indicate that 64% of the invasive strains of meningo B are divided among these 6 complexes, whereas, at the present time, 50 complexes have been described (19% of the European strains not having been assigned to a determined complex).

The table below (Table II) provides further details concerning these 163 strains and indicates in parentheses the previous nomenclature or names of the corresponding MLEE (multi electrophoretic enzyme) complexes or electrophoretic (ET) complexes:

lgtC, lgtE and lgtH; lgtF; lgtG and lpt6; lpt3 and lot3. This analysis made it possible to predict the structure of the LOS in the 6 major epidemiological complexes of meningococcus B. The results are given in FIG. 2. It will be noted that the genotyping results for certain strains are such that it had to be deduced that such a strain is capable of manufacturing several types of LOS. The LOS of such a strain may thus be classed into several categories. To conclude, this explains, for example, why a strain can be compatibilized in several categories of α chain.

The results of the genotyping relating to 3 of the 4 genes involved in the biosynthesis of the inner core and acting on its variability (i.e. lgtG, lpt6 and lpt3) and also the structure deduced therefrom are presented in detail in Table III below:

TABLE III

Combination between clonal complexes and phenotype/genotype of the inner core

| | | | | ST complexes | | | | | | Sum | |
| --- | --- | --- | --- | --- | --- | --- | --- | --- | --- | --- | --- |
| Distribution of the 6 major epidemiological complexes in the invasive strains of serogroup B | | | | 41/44 (lineage III) 25% | 32 (ET-5) 20% | 269 7% | 18 4% | 8 (cluster A4) 4% | 11 (ET-37) 4% | of the strains 64% | |
| No substitution | lpt3− | lgtG− | lpt6− | | | | | 6 | | 7 4.3% | No substitution |
| | lpt3+ deleted lpt3− | lgtG Off | lpt6− | 1 | | | | | | | |
| Glu-3 | lpt3− | lgtG On | lpt6− | | | | | | | 10 | Glu-3 |
| | lpt3+ | lgtG On | lpt6− | | 9 | | | | 1 | 6.13% | |
| PEA-3 | lpt3+ | lgtG− | lpt6− | 33 | | 14 | | | | 92 | PEA-3 |
| | lpt3+ | lgtG Off | lpt6− | | 44 | | 1 | | | 56.44% | |
| PEA-3 | lpt3+ | lgtG− | lpt6+ | | | | | | | 32 | PEA-3 |
| PEA-6 | lpt3+ | lgtG Off | lpt6+ | | | | | 13 | 19 | 19.63% | PEA-6 |
| Glu-3 | lpt3− | lgtG On | lpt6+ | | | | | | | 21 | Glu-3 |
| PEA-6 | lpt3+ | lgtG On | lpt6+ | | | | | 13 | 8 | 12.88% | PEA-6 |
| PEA-6 | lpt3− | lgtG− | lpt6+ | | | | | | | 1 | PEA-6 |
| | lpt3− | lgtG Off | lpt6+ | | | | | | 1 | 0.60% | |
| Number of strains tested | | | | 34 | 53 | 14 | 7 | 28 | 27 | 163 | |

Moreover, the genotyping study relating to the lot3 gene reveals that the vast majority of the strains tested O-acetylate their LOS (lot3 gene present and "On").

BRIEF DESCRIPTION OF THE FIGURES

The patent or application file contains at least one drawing executed in color. Copies of this patent or patent application publication with color drawing(s) will be provided by the Office upon request and payment of the necessary fee.

Figure 1:
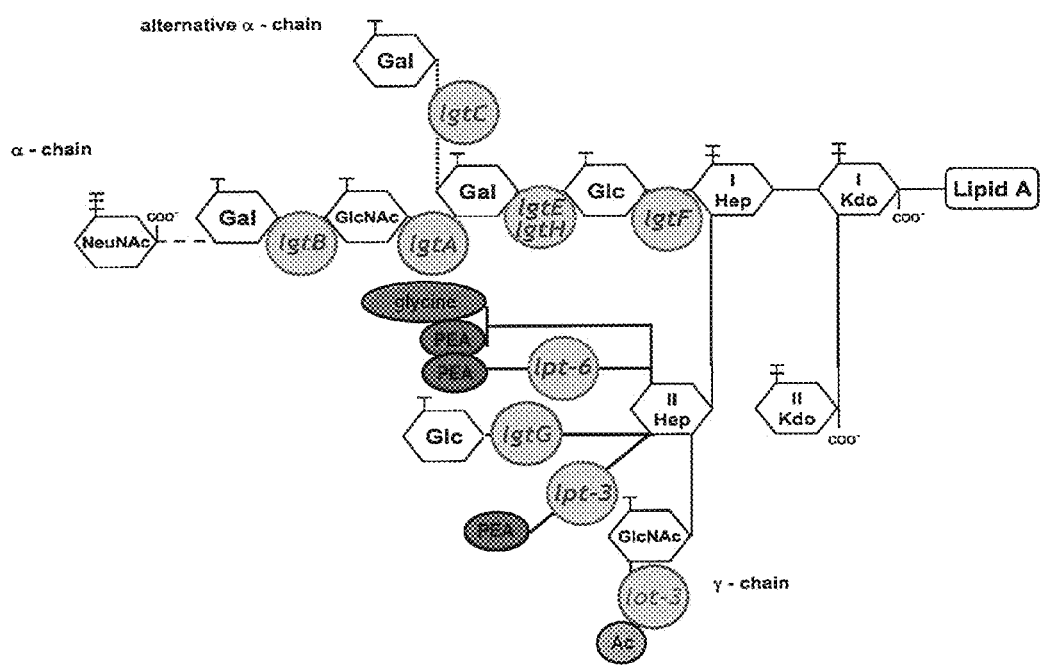
FIG. 1 shows the structure of the LOS of N. meningitidis, the various sites at which the variability is expressed and also the levels of intervention of the genes.
Figure 2:
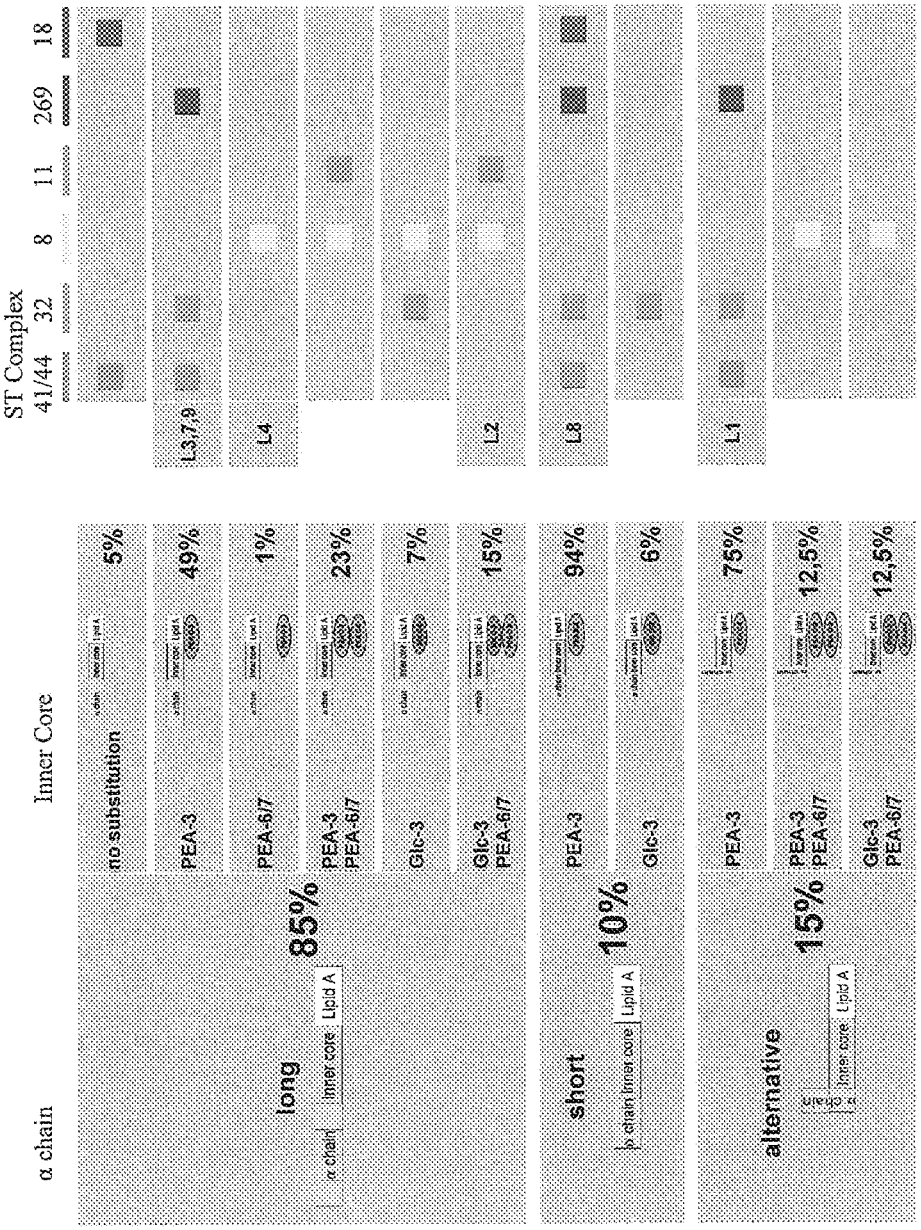
FIG. 2 shows the results of the genotyping analysis of the lgtA, lgtB, lgtC, lgtE and lgtH; lgtF; lgtG and lpt6; lpt3 and lot3 genes that participate in the biosynthesis of LPS.

In coherence with the results of the genotyping study relating to the lgtG, lpt6 and lpt3 genes, a vaccine composition intended to prevent or treat infections caused by N. meningitidis is proposed, which comprises one or more LOSs of N. meningitidis; this being (i) so as to treat or prevent at least 70%, advantageously at least 75% and preferably at least 80% of infections caused by N. meningitidis, especially caused by N. meningitidis serogroup B or

TABLE II

| Complex | Number of strains | Origin (number of countries) | Period of isolation | Main source |
| --- | --- | --- | --- | --- |
| ST-41/44 (lineage III) | 34 | 9 | 1963-1994 | D. Caugant/ D. Martin |
| ST-32 (ET-5) | 53 | 10 | 1981-1996 | D. Caugant |
| ST-269 | 14 | 2 | 1988-2007 | D. Caugant |
| ST-18 | 7 | 2 | 1985-2005 | D. Caugant |
| ST-8 (cluster A4) | 28 | 12 | 1967-1994 | D. Caugant/ M. Diggle |
| ST-11 (ET-37) | 27 | 7 | 1969-1988 | D. Caugant/ M. Diggle |

The genes participating in the biosynthesis of the LPS that were analyzed by genotyping are the following: lgtA, lgtB, (ii) to vaccinate against 75 to 90%, advantageously from 75 to 100%, preferably from 80 to 90% and most preferably particularly from 80 to 100% of infections caused by *N. meningitidis*, especially of serogroup B.

To this end, the choice of an LOS bearing an α chain of L6 type and a heptose II residue of the inner core substituted in the O-3 position with a phosphoethanolamine residue proves to be particularly advantageous. Now, as reported previously in Table I above, the L6 immunotype strains bear only one PEA substituent in position 6/7.

Thus, when the vaccine composition comprises only one LOS, the latter has to be necessarily optimized. When the vaccine composition comprises at least two LOSs, one of the at least two LOSs must necessarily have been optimized; the second may be a natural (non-optimized) LOS.

In order to be able to manufacture a vaccine according to the invention, three strain manufacturing processes are first proposed, listed as follows:

(i) a process of making a strain of *N. meningitidis* exhibiting a lipooligosaccharide (LOS) in particular constituted by (comprising) a lipid A, an inner core, an α chain of L6 type, in which the heptose II residue of the inner core bears in position O-3 and in position O-6 or O-7 a phosphoethanolamine (PEA) substituent; wherein an *N. meningitidis* strain of immunotype L6 is modified such that it expresses an lpt3 gene;

(ii) a process of making an *N. meningitidis* strain exhibiting a lipooligosaccharide (LOS) in particular constituted by (comprising) a lipid A, an inner core, an α chain of L6 type, in which the heptose II residue of the inner core bears in position O-3 a phosphoethanolamine (PEA) substituent and does not bear a PEA substituent in positions O-6 and O-7; wherein an *N. meningitidis* strain of immunotype L6 is modified such that it expresses an lpt3 gene and such that it no longer expresses the lpt6 gene; and (iii) a process of making an *N. meningitidis* strain exhibiting a lipooligosaccharide (LOS) in particular constituted by a lipid A, an inner core, an α chain of L8 type, in which the heptose II residue of the inner core bears in position O-3 and in position O-6 or O-7 a phosphoethanolamine (PEA) substituent; wherein an *N. meningitidis* strain of immunotype L8 is modified such that it expresses an lpt6 gene.

The *N. meningitidis* serogroup against which it is imperative to propose a vaccine in priority is the serogroup B (vaccines against the other prevalent serogroups A, C, Y and W135 are already available). Purification of the LOS from a strain of serogroup B may lead to a product containing the undesirable residual B capsule in the vaccine. To overcome these difficulties, it has now been found that an ad hoc LOS derived from strains of serogroup A can satisfy the needs in terms of vaccination against the serogroup B. This is why, in the manufacturing processes (i) and (ii) according to the invention, an *N. meningitidis* strain of immunotype L6, serogroup A is preferably used as starting strain.

A strain that may be used in the manufacturing processes may express an LOS bearing a non-detoxified lipid A. In particular, the msbB gene may be functional.

A strain of this type is the strain C708 filed on 11 Mar. 2008 at the Collection Nationale de Culture de Microorganisme, 25 rue du Dr Roux 75015 Paris, according to the terms of the treaty of Budapest. This strain bears the order number CNCM 1-3942. This strain bears, inter alia, an active lgtA gene (gene switched "ON"); an lgtB gene—(non-functional gene); an lgtG gene (switched "Off"); a truncated lpt3 gene; an active lpt6 gene; an active lot3 gene; and an active msbB gene.

The strain C708 comprises a truncated lpt3 gene. To modify it such that the LOS bears a PEA substituent in position 03, the functionality of the lpt3 gene can be restored, especially by homologous recombination using a complete (full-length) lpt3 gene. When this strain is used in process (ii) according to the invention, it is also appropriate to deactivate the lpt6 gene so as to obtain a strain that no longer expresses this gene. The deactivation of this gene may especially be achieved by total or partial deletion of the lpt6 gene or alternatively by insertion of a non-pertinent sequence into the gene, for example an antibiotic-resistant gene.

According to another aspect, a subject of the invention is also:

(i) an *N. meningitidis* strain, especially of serogroup A, exhibiting a lipooligosaccharide (LOS) in particular constituted by a lipid A, an inner core, an α chain of L6 type, in which the heptose II residue of the inner core bears in position O-3 and in position O-6 or O-7 a phosphoethanolamine (PEA) substituent;

(ii) an *N. meningitidis* strain of serogroup A, which exhibits a lipooligosaccharide (LOS) in particular constituted by a lipid A, an inner core, an α chain of L6 type, in which the heptose II residue of the inner core bears in position O-3 a phosphoethanolamine (PEA) substituent and does not bear a PEA substituent in positions O-6 and O-7;

(iii) a lipooligosaccharide (LOS) of *N. meningitidis* in particular constituted by a lipid A that may or may not be detoxified, an inner core, an α chain of L6 type, in which the heptose II residue of the inner core bears in position O-3 and in position O-6 or O-7 a phosphoethanolamine (PEA) substituent; and (iv) a lipooligosaccharide (LOS) of *N. meningitidis* in particular constituted by a non-detoxified lipid A, an inner core, an α chain of L6 type, in which the heptose II residue of the inner core bears in position O-3 a phosphoethanolamine (PEA) substituent and does not bear a PEA substituent in positions O-6 and O-7.

Advantageously, the strains according to the invention have a functional lot3 gene, in "On" phase variation such that the LOS that they produce is O-acetylated, at least partially, on their γ chain. The strains according to the invention may bear a functional msbB gene and/or express an LOS in particular constituted by a non-detoxified lipid A.

Advantageously, an LOS according to the invention bears a γ chain that is O-acetylated, at least partially.

An LOS included in the composition of a vaccine according to the invention may be prepared according to one of the following three processes:

(i) a process for preparing a lipooligosaccharide (LOS) of *N. meningitidis* in particular constituted by a lipid A, an inner core, an α chain of L6 type, in which the heptose II residue of the inner core bears in position O-3 and in position O-6 or O-7 a phosphoethanolamine (PEA) substituent; wherein (a) a strain obtained from the manufacturing process (i) according to the invention or the strain (i) according to the invention is cultured, and (b) the LOS is harvested from the culture obtained in step (a);

(ii) a process for preparing a lipooligosaccharide (LOS) of *N. meningitidis* in particular constituted by a lipid A, an inner core, an α chain of L6 type, in which the heptose II residue of the inner core bears in position O-3 a phosphoethanolamine (PEA) substituent and does not bear a PEA substituent in positions O-6 and O-7; wherein (a) a strain obtained from the manufacturing process (ii) or the strain (ii) according to the invention is cultured, and (b) the LOS is harvested from the culture obtained in step (a); and (iii) a process for preparing a lipooligosaccharide (LOS) of *N. meningitidis* in particular constituted by a lipid A, an inner core, an α chain of L8 type, in which the heptose II residue of the inner core bears in position O-3 and in position O-6 or O-7 a phosphoethanolamine (PEA) substituent; wherein (a) a strain obtained from the manufacturing process (iii) is cultured and (b) the LOS is harvested from the culture obtained in step (a).

In each of the three preparation processes, the LOS may be harvested either in a form combined with outer membrane vesicles (OMVs), or extracted so as to be purified thereafter.

The first case amounts to harvesting OMVs that contain LOS. Such OMVs may be isolated according to many techniques. See, for example, WO 04/014417, Fredriksen et al., NIPH Annals (1991) 14: 67-79; Zollinger et al., J. Clin Invest (1979) 63: 836-848; Saunders et al., Infect. Immun. (1999) 67: 113-119; and Drabick et al., Vaccine (1999) 18: 160-172. These techniques may be divided into two major groups; those using deoxycholate (DOC) at a concentration of about 0.5%; and those using lower concentrations or no DOC at all. The techniques that dispense with DOC have the advantage of concentrating the LOS in the OMVs (about 10-fold more LOS than in the OMVs extracted via a technique using DOC). However, the techniques using low doses of DOC may also be advantageous in that they can reduce the residual toxicity of the LOS while at the same time making it possible to obtain advantageous concentrations of LOS. Once extracted, the OMVs can be purified by ultrafiltration or diafiltration techniques known to those skilled in the art and described, for example, in Frasch et al. "Outer membrane protein vesicle vaccines for meningococcal disease" in Methods in Molecular Medicine, vol. 66, Meningococcal Vaccines: Methods and Protocols (2001): 81-107 (Edited by A J. Pollard and M. C. Maiden, Humana Press Totowa, N.J.).

In the second case, the LOS is extracted from a bacterial culture and then purified according to standard methods. Many purification processes are described in the literature. By way of example, mention is made of Gu & Tsaï, 1993, Infect. Immun. 61 (5): 1873, Wu et al., 1987, Anal. Biochem. 160: 281 and U.S. Pat. No. 6,531,131. An LPS preparation can also be quantified by using known techniques. A practical method consists in assaying the KDO by HPAEC-PAD chromatography (high performance anion exchange chromatography).

Detoxification of the LOS

For incorporation into a vaccine, the LOS needs to be detoxified. The toxicity of the LOS is due to its lipid A. However, it is neither imperative to remove the lipid A in its entirety; nor to modify it, for example by mutation (e.g. msbB minus mutation). In fact, since the toxicity is more particularly linked to a supramolecular conformation conferred by all the fatty acid chains borne by the disaccharide nucleus of the lipid, according to one advantageous embodiment, it is sufficient to act on these chains.

The detoxification can be obtained according to various approaches: chemical, enzymatic or genetic or alternatively by complexation with a peptide analog of polymyxin B or alternatively by incorporation/formulation into liposomes.

The level of detoxification of the LOS can be assessed inter alia according to one of the two following standard tests:

the pyrogenic test in rabbits. This test, the calculations and the reading thereof have been implemented according to the principles set out in the European Pharmacopoeia (Edition 6.0, paragraph 2.6.8.).

the LAL test (Limulus Amebocyte Lysate) implemented according to the principles set out in the European Pharmacopoeia (Edition 6.0, paragraph 2.6.14.).

Detoxification Via the Chemical Route

The chemical approach consists in treating the LOS with a chemical agent. According to one particular embodiment, the LOS is subjected to mild acid hydrolysis with acetic acid which removes the lipid A and also the branched KDO(s) when it (they) is (are) present in the LOS structure. Such a treatment is, for example, described in Gu & Tsai Infect. Immun. (1993) 61: 1873. According to an alternative and preferred embodiment, the LOS is subjected to a de-O-acylation, preferably a primary de-O-acylation, i.a. by treatment with hydrazine, which hydrolyzes the esterified primary fatty acid chains of the lipid A. Such a treatment is, for example, described in U.S. Pat. No. 6,531,131, Gupta et al, Infect. Immun. (1992) 60 (8): 3201 and Gu et al, Infect. Immun. (1996) 64 (10): 4047.

Detoxification Via the Enzymatic Route

The enzymatic approach consists in placing the LOS in the presence of lipases capable of digesting the esterified fatty acid chains of the lipid A. Such lipases are produced by the amoeba *Dictyostelium discoideum*. According to one particularly advantageous embodiment, the amoeba and a Gram-negative bacterium that can be phagocytosed by the amoeba, such as *N. meningitidis*, are cultured together (coculture). The supernatant is then recovered and the LOS is extracted from the supernatant which is then free of fatty acid chains. It may also be an acyloxyacyl hydrolase produced by certain human cells (patent WO 87/07297 Munford R.) or by *Salmonella typhimurium* (Trent et al 2001 J. Biol. Chem. 276: 9083-9092; Reynolds et al. 2006 J. Biol. Chem. 281: 21974-21987) (enzyme encoded by the PagL or LpxR genes in the latter case).

Detoxification Via the Genetic Route

The genetic approach consists in using an LOS produced by a bacterial strain of which the genotype is such that the entity of the LOS normally responsible for its toxicity (lipid A, and more particularly the lipid tails of lipid A) has a greatly reduced or even nonexistent degree of toxicity. Such a bacterial strain can be conveniently obtained by mutation. Starting from a wild-type strain (i.e. a strain producing a toxic LOS), this then involves inactivating, by mutation, certain genes involved in the biosynthesis of the fatty acid chains, or in the attachment thereof to the disaccharide nucleus of lipid A. Thus, it is possible to envision inactivating the lpxL1 or lpxL2 genes (also called htrB1/htrB2) of *N. meningitidis* or equivalents thereof in other species (for example, the equivalents of the meningococcal lpxL1 and lpxL2 genes are respectively called msbB or lpxM and htrB or lpxL in *E. coli*.). A mutation that inactivates one of these genes results in an LOS devoid of one or of two secondary acyl chains. lpxL1 or L2 mutants of *N. meningitidis* or of *Haemophilus influenzae* are in particular described in patent applications WO 00/26384, US 2004/0171133 and WO 97/019688. In *N. meningitidis*, the endogenous lpxA gene can also be replaced with the homologous gene originating from *E. coli* or *Pseudomonas aeruginosa*. The fatty acid chains thereof are modified, resulting in a less toxic lipid A (Steeghs et al, Cell. Microbiol. (2002) 4 (9): 599). The genetic approach is favored when the LOS is purified in the form of OMVs.

LOS Detoxified by Complexation with a Peptide Analog of Polymyxin B A fourth approach consists in complexing the LOS with a peptide analog of polymyxin B, as is, for example, described in patent application WO 06/108586. The LOS that is complexed and consequently detoxified is called endotoxoid.

The polymyxin B analog included in the composition of an endotoxoid that is useful for the purposes of the present invention may be any peptide that is capable of detoxifying the LPS by simple complexation. Such peptides are especially described in patent or patent applications U.S. Pat. No. 6,951,652, EP 976 402 and WO 06/108 586.

Thus, an advantageous peptide may be the peptide of formula (I)

  (SEQ ID NO: 1), in which:
A is a peptide of 2 to 5 and preferably 3 or 4 amino acid residues, in which at least 2 amino acid residues are independently chosen from Lys, Hyl (hydroxylysine), Arg and His;
B is a peptide of 3 to 7 and preferably 4 or 5 amino acid residues, which comprises at least two and preferably three amino acid residues chosen from Val, Leu, Ile, Phe, Tyr and Trp; and
C is optional (this position may or may not be empty) and is an amino acid residue or a peptide formed from 2 to 3 amino acid residues;
on condition that the cationic amino acid/hydrophobic amino acid ratio in the peptide of formula I is from 0.4 to 2, advantageously from 0.5 to 1.2 or 1.5, preferably from 0.6 to 1; better still from 0.6 to 0.8; for example 0.75.

Preferably, in the peptide of formula (I), position C is an empty position.

Particular examples of the peptide of formula (I) are the following peptides:

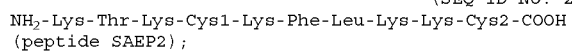

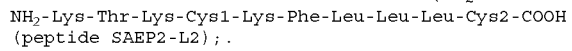

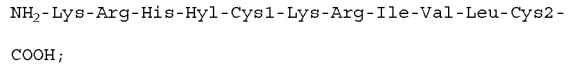

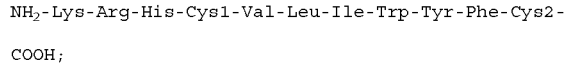

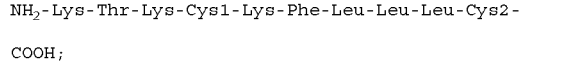
and

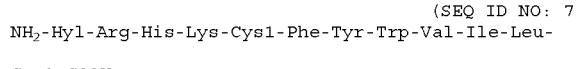

The peptides of formula (I) may be in monomer form or, preferably, in parallel or antiparallel dimer form.

In general, use may also be made of a dimeric peptide of formula (II)

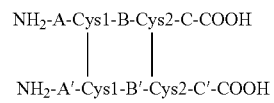

in which the two Cys1 residues are linked together via a disulfide bridge and the two Cys2 residues are linked together via a disulfide bridge;
or of formula (III)

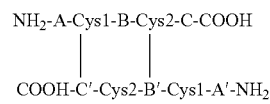

in which the Cys1 residues are linked to the Cys2 residues via peptide inter-chain disulfide bridges;
in which formulae (II) and (III):
A and A' are, independently, a peptide of 2 to 5 and preferably 3 or 4 amino acid residues, in which at least 2 amino acid residues are independently chosen from Lys, Hyl (hydroxylysine), Arg and His;
B and B' are, independently, a peptide of 3 to 7 and preferably 4 or 5 amino acid residues, which comprise at least two and preferably three amino acid residues independently chosen from Val, Leu, Ile, Phe, Tyr and Trp; and
C and C' are optional (these positions may or may not be empty) and are, independently, an amino acid residue or a peptide of 2 to 3 amino acid residues;
on condition that the cationic amino acid/hydrophobic amino acid ratio in the dimer of formula (II) or (III) is from 0.4 to 2, advantageously from 0.5 to 1.2 or 1.5, preferably from 0.6 to 1 and better still from 0.6 to 0.8; for example. 0.75.

Advantageously, A and A' are, independently, a peptide of 2 to 5 and preferably 3 or 4 amino acid residues, in which at least one and preferably 2 amino acid residues are independently chosen from Lys, Hyl, Arg and His; and, where appropriate, those that are not chosen from Lys, Hyl, Arg and His ("the remaining amino acid residues") being chosen from the group of uncharged, polar or nonpolar amino acid residues; preferably Thr, Ser and Gly; most particularly preferably Thr.

When A and A' comprise 3 amino acid residues, each of them may be a cationic residue; or alternatively, two of the three residues are cationic amino acids, whereas the remaining residue is chosen from the group of uncharged, polar or nonpolar amino acid residues; preferably Thr, Ser and Gly; most particularly preferably Thr.

When A and A' comprise 4 amino acid residues, it is preferable for two or three of the four residues to be chosen from the groups of cationic amino acid residues as defined above, whereas the remaining residue(s) is(are) chosen from the group of uncharged, polar or nonpolar amino acid residues as defined above.

When A and A' comprise 5 amino acid residues, it is preferred for three or four of the five residues to be chosen from the groups of cationic amino acid residues as defined above, whereas the remaining residue(s) is(are) chosen from the group of uncharged, polar or nonpolar amino acid residues as defined above.

Advantageously, B and B' are, independently, a peptide of 3 to 7 and preferably 4 or 5 amino acid residues, which comprises at least two and preferably three amino acid residues independently chosen from Val, Leu, Ile, Phe, Tyr and Trp; preferably Leu, Ile and Phe; and, where appropriate, those that are not chosen from Val, Leu, Ile, Phe, Tyr and Trp ("the remaining amino acid residues") being chosen independently from the group formed by Lys, Hyl, Arg and His. As may readily be understood, B and B' may comprise up to 7 amino acid residues independently chosen from Val, Leu, Ile, Phe, Tyr and Trp.

Advantageously, B and B' comprise the sequence -X1-X2-X3-, in which X1 and X2; X2 and X3; or X1, X2 and X3 are independently chosen from Val, Leu, Ile, Phe, Tyr and Trp; preferably from Leu, Ile and Phe. In one preferred embodiment, the sequence -X1-X2-X3- comprises the Phe-Leu unit.

The particular embodiments of B and B' include:
(i) the sequence -X1-X2-X3- in which:
X1 is Lys, Hyl, His or Arg, preferably Lys or Arg; preferably Lys;
X2 is Phe, Leu, Ile, Tyr, Trp or Val; preferably Phe or Leu; more particularly preferably Phe; and
X3 is Phe, Leu, Ile, Tyr, Trp or Val; preferably Phe or Leu; more particularly preferably Leu; and
(ii) where appropriate, the amino acid residues are each independently chosen from the group formed by Val, Leu, Ile, Phe, Tyr, Trp, Lys, Hyl, Arg and His; preferably Val, Leu, Ile, Phe, Tyr and Trp; more particularly preferably Leu, Ile and Phe.

When B and B' comprise more than 4 nonpolar amino acid residues, A and A' preferably comprise at least 3 positively charged amino acid residues.

In C and C', the amino acid residues may be any amino acid residue, on condition that the cationic amino acid residues/hydrophobic amino acid residues ratio remains in the indicated range. Advantageously, they are independently chosen from uncharged, polar or nonpolar amino acid residues, the latter being preferred. However, preferably, the positions C and C' are empty positions.

Consequently, a preferred class of the dimers is of formula (IV)

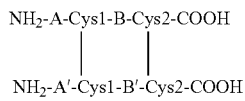

in which the two Cys1 residues are linked together via a disulfide bridge and the two Cys2 residues are linked together via a disulfide bridge;
or of formula (V)

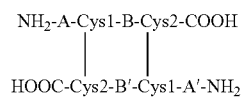

in which the Cys1 residues are linked to the Cys2 residues via peptide inter-chain disulfide bridges;
in which formulae (IV) and (V), in which A, A', B and B' are as described above; on condition that the cationic amino acid/hydrophobic amino acid ratio in the dimer of formula (IV) or (V), is from 0.4 to 2, advantageously from 0.5 to 1.2 or 1.5, preferably from 0.6 to 1 and better still from 0.6 to 0.8; for example 0.75.

In formulae (II) to (V), A and A' are preferably identical. This is likewise the case as regards B and B', on the one hand, and C and C', on the other hand. A dimer of formula (II) to (V), in which A and A'; B and B'; and C and C' are identical in pairs, is designated as a homologous dimer.

For these dimers, mention may be made, for example, of the parallel and antiparallel dimers formed from the peptide SAEP2-L2 (SEQ ID NO: 3):

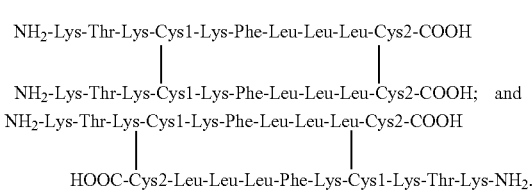

The endotoxoid that is useful for the purposes of the present invention may advantageously be characterized by an LOS/peptide mole ratio from 1/1.5 to 1/0.5, preferably from 1/1.2 to 1/0.8, and most particularly preferably from 1/1.1 to 1/0.9, e.g. 1/1.

LOS in Detoxified Liposomes

When the LOS is formulated in liposomes, it does not appear to be necessarily required to detoxify it beforehand. This is because LOS in liposomes—i.e. associated with the lipid bilayer forming the liposomes—may experience a very substantial decrease in toxicity. The size of this decrease, which can be as much as a substantial loss, depends partly on the nature of the components forming the liposome. Thus, when positively charged components (components of cationic nature) are used, the loss of toxicity may be greater than with uncharged (neutral) or anionic components.

The term "liposomes" is intended to mean a synthetic entity, preferably a synthetic vesicle, formed of at least one lipid bilayer membrane (or matrix) enclosing an aqueous compartment. For the purposes of the present invention, the liposomes may be uni-lamellar (a single bilayer membrane) or multi-lamellar (several membranes layered like an onion). The lipids constituting the bilayer membrane comprise a non-polar region which, typically, is made of chain(s) of fatty acids or of cholesterol, and a polar region, typically made of a phosphate group and/or of tertiary or quaternary ammonium salts. Depending on its composition, the polar region may, in particular at physiological pH (pH≈7) carry either a negative (anionic lipid) or positive (cationic lipid) net (overall) surface charge, or not carry a net charge (neutral lipid).

For the purposes of detoxifying the LOS, the liposomes may be liposomes of any type; in particular, they may be in particular constituted of any lipid known to be of use in the production of liposomes. The lipid(s) that go(es) to make up the composition of the liposomes may be neutral, anionic or cationic lipid(s); the latter being preferred. These lipids may be of natural origin (plant or egg extraction products, for example) or synthetic origin; the latter being preferred. The liposomes may also be in particular constituted of a mixture of these lipids; for example, of a cationic or anionic lipid and of a neutral lipid, as a mixture. In the latter two cases, the neutral lipid is often referred to as co-lipid. According to one advantageous mixture embodiment, the charged (cationic or anionic) lipid: neutral lipid mole ratio is between 10:1 and 1:10, advantageously between 4:1 and 1:4, preferably between 3:1 and 1:3, limits included.

With regard to the neutral lipids, mention is made, by way of example, of: (i) cholesterol; (ii) phosphatidylcholines such as, for example, 1,2-diacyl-sn-glycero-3-phosphocholines, e.g. 1,2-dioleoyl-sn-glycero-3-phosphocholine (DOPC), and also 1-acyl-2-acyl-sn-glycero-3-phosphocholines of which the acyl chains are different than one another (mixed acyl chains); and (iii) phosphatidylethanolamines such as, for example, 1,2-diacyl-sn-glycero-3-phosphoethanolamines, e.g. 1,2-dioleoyl-sn-glycero-3-phosphoethanolamine (DOPE), and also 1-acyl-2-acyl-sn-glycero-3-phosphoethanolamines bearing mixed acyl chains.

With regard to the anionic lipids, mention is made, by way of example, of: (i) cholesteryl hemisuccinate (CHEMS); (ii) phosphatidylserines such as 1,2-diacyl-sn-glycero-3-[phospho-L-serine]s, e.g. 1,2-dioleoyl-sn-glycero-3-[phospho-L-serine] (DOPS), and 1-acyl-2-acyl-sn-glycero-3-[phospho-L-serine]s bearing mixed acyl chains; (iii) phosphatidylglycerols such as 1,2-diacyl-sn-glycero-3-[phospho-rac-(1-glycerol)]s, e.g. 1,2-dioleoyl-sn-glycero-3-[phospho-rac-(1-glycerol)] (DOPG), and 1-acyl-2-acyl-sn-glycero-3-[phospho-rac-(1-glycerol)]s bearing mixed acyl chains; (iv) phosphatidic acids such as 1,2-diacyl-sn-glycero-3-phosphates, e.g. 1,2-dioleoyl-sn-glycero-3-phosphate (DOPA), and 1-acyl-2-acyl-sn-glycero-3-phosphates bearing mixed acyl chains; and (v) phosphatidylinositols such as 1,2-diacyl-sn-glycero-3-(phosphoinositol)s, e.g. 1,2-dioleoyl-sn-glycero-3-(phosphoinositol) (DOPI), and 1-acyl-2-acyl-sn-glycero-3-(phosphoinositol)s bearing mixed acyl chains.

With regard to the cationic lipids, mention is made, by way of example, of:
(i) lipophilic amines or alkylamines such as, for example, dimethyldioctadecylammonium (DDA), trimethyldioctadecylammonium (DTA) or structural homologs of DDA and of DTA [these alkylamines are advantageously used in the form of a salt; mention is made, for example, of dimethyldioctadecylammonium bromide (DDAB)];
(ii) octadecenoyloxy(ethyl-2-heptadecenyl-3-hydroxyethyl) imidazolinium (DOTIM) and structural homologs thereof;
(iii) lipospermines such as N-palmitoyl-D-erythrosphingosyl-1-O-carbamoylspermine (CCS) and dioctadecylamidoglycylspermine (DOGS, transfectam);
(iv) lipids incorporating an ethylphosphocholine structure, such as cationic derivatives of phospholipids, in particular phosphoric ester derivatives of phosphatidylcholine, for example those described in patent application WO 05/049080 and including, in particular:
    1,2-dimyristoyl-sn-glycero-3-ethylphosphocholine,
    1,2-dipalmitoyl-sn-glycero-3-ethylphosphocholine,
    1,2-palmitoyloleoyl-sn-glycero-3-ethylphosphocholine,
    1,2-distearoyl-sn-glycero-3-ethylphosphocholine (DSPC),
    1,2-dioleyl-sn-glycero-3-ethylphosphocholine (DOEPC or EDOPC or ethyl-DOPC or ethyl PC),
    and also structural homologs thereof;
(v) lipids incorporating a trimethylammonium structure, such as N-(1-[2,3-dioleyloxy]propyl)-N,N,N-trimethylammonium (DOTMA) and structural homologs thereof and those incorporating a trimethylammonium propane structure, such as 1,2-dioleyl-3-trimethylammonium propane (DOTAP) and structural homologs thereof; and also lipids incorporating a dimethylammonium structure, such as 1,2-dioleyl-3-dimethylammonium propane (DODAP) and structural homologs thereof; and
(vi) cationic derivatives of cholesterol, such as 3β-[N—(N', N'-dimethylaminoethane)-carbamoyl] cholesterol (DC-Chol) or other cationic derivatives of cholesterol, such as those described in U.S. Pat. No. 5,283,185, and in particular cholesteryl-3β-carboxamidoethylenetrimethylammonium iodide, cholesteryl-3P3-carboxyamidoethyleneamine, cholesteryl-3β-oxysuccinamidoethylenetrimethylammonium iodide and 3β-[N-(polyethyleneimine)carbamoyl]cholesterol.

The term "structural homologs" signifies lipids which have the characteristic structure of the reference lipid while at the same time differing therefrom by virtue of secondary modifications, especially in the nonpolar region, in particular of the number of carbon atoms and of double bonds in the fatty acid chains.

These fatty acids, which are also found in the neutral and anionic phospholipids, are, for example, dodecanoic or lauric acid (C12:0), tetradecanoic or myristic acid (C14:0), hexadecanoic or palmitic acid (C16:0), cis-9-hexadecanoic or palmitoleic acid (C16:1), octadecanoic or stearic acid (C18:0), cis-9-octadecanoic or oleic acid (C18:1), cis,cis-9,12-octadecadienoic or linoleic acid (C18:2), cis-cis-6,9-octadecadienoic acid (C18:2), all-cis-9,12,15-octadecatrienoic or α-linolenic acid (C18:3), all-cis-6,9,12-octadecatrienoic or γ-linolenic acid (C18:3), eicosanoic or arachidic acid (C20:0), cis-9-eicosenoic or gadoleic acid (C20:1), all-cis-8,11,14-eicosatrienoic acid (C20:3), all-cis-5,8,11,14-eicosatetraenoic or arachidonic acid (C20:4), all-cis-5,8,11,14,17-eicosapentaneoic acid (C20:5), docosanoic or behenic acid (C22:0), all-cis-7,10,13,16,19-docosapentaenoic acid (C22:5), all-cis-4,7,10,13,16,19-docosahexaenoic acid (C22:6) and tetracosanoic or lignoceric acid (C24:0).

According to one particular embodiment, a mixture of cationic lipid and neutral lipid is used. By way of example, mention is made of:
    a mixture of DC-chol and DOPE, in particular in a DC-chol:DOPE mole ratio ranging from 10:1 to 1:10, advantageously from 4:1 to 1:4, preferably from approximately 3:1 to 1:3;
    a mixture of ethyl-DOPC and cholesterol, in particular in an ethyl-DOPC:cholesterol mole ratio ranging from 10:1 to 1:10, advantageously from 4:1 to 1:4, preferably from approximately 3:1 to 1:3; and
    a mixture of ethyl-DOPC and DOPE, in particular in an ethyl-DOPC:DOPE mole ratio ranging from 10:1 to 1:10, advantageously from 4:1 to 1:4, preferably from approximately 3:1 to 1:3.

According to one advantageous method of preparation, in an initial step, a dry lipid film is prepared with all the compounds that go to make up the composition of the liposomes. The lipid film is then rein particular constituted in an aqueous medium, in the presence of LOS, for example in a lipid:LOS mole ratio of 100 to 500, advantageously of 100 to 400, preferably of 200 to 300, most particularly preferably of approximately 250. In general, it is considered that this same mole ratio should not substantially vary at the end of the method of preparing the LOS liposomes.

In general, the reconstitution step in an aqueous medium results in the spontaneous formation of multilamellar vesicles, the size of which is subsequently homogenized by gradually decreasing the number of lamellae by extrusion, for example using an extruder, by passing the lipid suspension, under a nitrogen pressure, through polycarbonate membranes having decreasing pore diameters (0.8, 0.4, 0.2 μm). The extrusion process can also be replaced with another process using a detergent (surfactant) which disperses lipids. This detergent is subsequently removed by dialysis or by adsorption onto porous polystyrene microbeads with a particular affinity for detergent (BioBeads).

When the surfactant is removed from the lipid dispersion, the lipids reorganize in a double layer.

At the end of the incorporation of the LOS into liposomes, a mixture in particular constituted of ad hoc liposomes and of LOS in free form may commonly be obtained. Advantageously, the liposomes are then purified in order to be rid of the non-detoxified LPS in free form.

Conjugation of LOS

In a vaccine according to the invention, the LOS is advantageously in the form of a LOS/polypeptide carrier conjugate, in particular when it is not in the form of OMVs or liposomes.

The carrier polypeptide can be any carrier polypeptide, oligopeptide or protein in use in the conjugated vaccines field; and in particular pertussis, diphtheria or tetanus toxoid, the diphtheria toxin mutant named CRM197, a bacterial OMP or a bacterial protein complex (for example, *N. meningitidis* OMPC (outer-membrane protein Complex)), *Pseudomonas* exotoxin A, *Haemophilus influenzae* lipoprotein D, *Streptococcus pneumoniae* pneumolysine, *Bordetella pertussis* filamentous hemagglutinin and the subunit B of the human transferrin receptor of *N. meningitidis* (TbpB).

Many methods of conjugation exist in the technical field. Some are listed, for example, in patent applications EP 941 738 and WO 98/31393.

In general, the reactive groups of the LOS involved in the conjugation are those of the inner core or of lipid A. It may involve, inter alia, the acid function of the KDO, or else an aldehyde generated subsequent to an appropriate treatment on the disaccharide of lipid A. For example, a phosphatase treatment generates an aldehyde on the structure of the second glucosamine of lipid A from *N. meningitidis* (Brade H. (2002) J. Endotoxin Res. 8 (4): 295 Mieszala et al, (2003) Carbohydrate Res. 338: 167 and Cox et al, (2005) Vaccine 23 (5): 5054).

Advantageously, the method of conjugation makes use (i) of a bifunctional linking agent (linker) or (ii) of a spacer and of a linker.

For example, in the first case, the LOS is activated with a bifunctional coupling agent (linker) of formula R1-A-R2, such that the R2 radical reacts with a reactive group of the KDO or of the lipid A in order to obtain an activated LOS; the activated LOS is then conjugated with the polypeptide such that the R1 substituent reacts with a functional group borne by the polypeptide, in order to obtain a conjugate.

For example, in the second case, the LOS is derivatized with a spacer of formula R3-B-R4 such that the R3 radical reacts with a reactive group of the KDO or of the lipid A in order to obtain a derivatized LOS; the derivatized LOS is then activated with a bifunctional coupling agent (linker) of formula R1-A-R2 such that the R2 radical reacts with the R4 radical in order to obtain a derivatized and activated LOS; finally, the derivatized and activated LOS is conjugated with the polypeptide such that the R1 radical reacts with a functional group borne by the polypeptide in order to obtain a conjugate.

In the second case, the process can also be carried out in the following way: the protein is derivatized with a spacer of formula R3-B-R4 such that the R4 radical reacts with a functional group borne by the polypeptide; the LOS is activated with a bifunctional linker of formula R1-A-R2 such that the R2 radical reacts with a reactive group of the KDO or of the lipid A, in order to obtain an activated LOS; and then the activated LOS is conjugated with the derivatized protein such that the R1 radical of the activated LOS reacts with the R3 radical of the derivatized polypeptide, in order to obtain a conjugate.

In the formula of the spacer, B may be a carbon chain, preferably carbonyl, alkyl or alkylene, for example C1 to C12. R3 and R4 may independently be a thiol or amine group or a residue bearing same, for example a hydrazide group, i.e. $NH_2$—NH—CO—. Compounds that may be used as a spacer have, for example, the formula $NH_2$—B—$NH_2$, or preferably $NH_2$—B—SH and $NH_2$—B—S—S—B'—$NH_2$. By way of particular example, mention is made of: cysteamine, cysteine, diamines, e.g. diaminohexane, adipic acid dihydrazide (ADH), urea and cystamine.

In the formula of the linker, A may be an aromatic or preferably aliphatic chain which is substituted or unsubstituted and which advantageously contains from 1 to 12 carbon atoms, preferably 3 to 8 carbon atoms. For example, A may be a C2 to C8 alkylene, a phenylene, a C7 to C12 aralkylene, a C2 to C8 alkyl, a phenyl, a C7 to C12 aralkyl, a C6 alkanoyloxy or a benzylcarbonyloxy, which may be substituted or unsubstituted.

The R2 radical is the functional group of the linker which creates the link with the LOS or with the derivatized LOS. Thus, R2 is a functional group which can react with a carboxyl, hydroxyl, aldehyde or amine group. If the linker must react with a hydroxyl, carboxyl or aldehyde group, R2 is preferably an amine group or a residue carrying an amine group, for example a hydrazide group, i.e. $NH_2$—NH—CO—. If the linker must react with an amine group, R2 is preferably a carboxyl, succinimidyl (e.g. N-hydroxysuccinimidyl) or sulfosuccinimidyl (e.g. N-hydroxysulfosuccinimidyl) group.

Thus, compounds that can be used as a linker may be chosen from adipic acid dihydrazide (ADH); sulfosuccinimidyl 6-(3-[2-pyridyldithio]propionamido)hexanoate (Sulfo-LC-SPDP); succinimidyl 6-(3-[2-pyridyldithio]propionamido)hexanoate (LC-SPDP); N-succinimidyl-S-acetyl thioacetate (SATA); N-succinimidyl 3-(2-pyridyldithio)propionate (SPDP), succinimidyl acetylthiopropionate (SATP); succinimidyl-4-(N-maleimidomethyl)cyclohexane-1-carboxylate (SMCC); maleimidobenzoyl-N-hydroxysuccinimide ester (MBS); N-succinimidyl (4-iodoacetyl)aminobenzoate (SIAB); succinimidyl 4-(p-maleimidophenyl)butyrate (SMPB); bromoacetic acid-N-hydroxysuccinimide (BANS) ester; dithiobis(succinimidylpropionate) (DTSSP); H-(γ-maleimidobutyryloxy)succinimide ester (GMBS); succinimidyl-4-(N-maleimidomethyl)cyclohexane-1-carboxylate; N-succinimidyl-4-(4-maleimidophenyl)butyrate; N-[β-maleimidocaproic acid] hydrazide (BMCH); N-succinimidyl-4-maleimidobutyrate; and N-succinimidyl-3-maleiimidobenzoate.

By way of example, it is proposed to use the acid function of the KDO in order to derivatize the LOS with ADH in the presence of a carbodiimide [e.g. 3-ethyl-(3-dimethylaminopropyl)carbodiimide hydrochloride (EDAC)]. The amine function thus introduced is then reacted with the carboxyl functions of the polypeptide, in the presence of EDAC, after having protected the amine functions of the latter (Wu et al (2005) Vaccine 23: 5177) or having converted them to acid functions (succinylation of the protein; Pavliakova et al, Infect. Immun. (1999) 67 (10): 5526).

Alternatively, it is proposed to use the acid function of the KDO in order to derivatize the LOS with cysteamine or cysteine in the presence of EDAC. The thiol function thus introduced is then reacted with the maleimide function of a homobifunctional linker, such as bismaleimidohexane; or a heterobifunctional linker, such as GMBS. In the first case, the maleimide function thus introduced is then reacted with the thiol functions of the polypeptide. In the second case, the succinimidyl function of the derivatized and activated LOS is reacted with the amine functions of the polypeptide.

Depending on the method of conjugation selected, the LOS and the polypeptide can be conjugated to one another in an LOS:polypeptide mole ratio of from $10^{-1}$ to $10^2$, advantageously from 1 to $10^2$, preferably from 1 to 50; most particularly preferably of approximately 20.

As stated previously, a subject of the invention is a pharmaceutical composition for combating infections caused by N. meningitidis, especially of serogroup B, which comprises:
(i) an N. meningitidis LOS, in particular constituted by a non-detoxified lipid A, an inner core, an α chain of L6 type, in which the heptose II residue of the inner core bears in position O-3 a phosphoethanolamine (PEA) substituent and does not bear a PEA substituent in positions O-6 and O-7 or an LOS obtained according to the preparation process (ii); and, optionally,
(ii) an N. meningitidis LOS in particular constituted by a lipid A, an inner core, an α chain of L6 type, in which the heptose II residue of the inner core bears in position O-3 and in position O-6 or O-7 a phosphoethanolamine (PEA) substituent or an LOS obtained according to the preparation process (i); and, optionally,
(iii) an N. meningitidis LOS in particular constituted by a lipid A, an inner core, an α chain of L6 or L8 type, in which the heptose II residue of the inner core bears in position O-6 or O-7 a phosphoethanolamine (PEA) substituent and does not bear a PEA substituent in position O-3.

A subject of the invention is also a pharmaceutical composition for combating infections caused by N. meningitidis, especially of serogroup B, which comprises an N. meningitidis LOS in particular constituted by a lipid A, an inner core, an α chain of L6 type, in which the heptose II residue of the inner core bears in position O-3 and in position O-6 or O-7 a phosphoethanolamine (PEA) substituent; or obtained according to preparation process (i).

As indicated previously, the latter composition may also comprise an LOS obtained according to preparation process (ii) or an N. meningitidis LOS in particular constituted by a lipid A, an inner core, an α chain of L6 type, in which the heptose II residue of the inner core bears in position O-3 a phosphoethanolamine (PEA) substituent and does not bear a PEA substituent in positions O-6 and O-7; and also an N. meningitidis LOS in particular constituted by a lipid A, an inner core, an α chain of L6 type, in which the heptose II residue of the inner core bears in position O-6 or O-7 a phosphoethanolamine (PEA) substituent and does not bear a PEA substituent in position O-3.

A subject of the invention is also a pharmaceutical composition for combating infections caused by N. meningitidis, especially of serogroup B, which comprises:
(i) an LOS of N. meningitidis, preferably of serogroup A, in particular constituted by a lipid A, an inner core, an α chain of L8 type, in which the heptose II residue of the inner core bears in position O-3 a phosphoethanolamine (PEA) substituent and does not bear a PEA substituent in positions O-6 and O-7; and
(ii) an N. meningitidis LOS, in particular constituted by a non-detoxified lipid A, an inner core, an α chain of L6 type, in which the heptose II residue of the inner core bears in position O-3 a phosphoethanolamine (PEA) substituent and does not bear a PEA substituent in positions O-6 and O-7 or an LOS obtained according to preparation process (ii); or an N. meningitidis LOS in particular constituted by a lipid A, an inner core, an α chain of L6 type, in which the heptose II residue of the inner core bears in position O-3 and in position O-6 or O-7 a phosphoethanolamine (PEA) substituent; or obtained according to preparation process (i).

In the latter composition, the LOS of point (i) may advantageously be the LOS of a strain of immunotype L8.

The invention also relates to a pharmaceutical composition against infections caused by N. meningitidis, especially of serogroup B, which comprises:
(i) an LOS of N. meningitidis, preferably of serogroup A, in particular constituted by a lipid A, an inner core, an α chain of L8 type, in which the heptose II residue of the inner core bears in position O-3 and in position O-6 or O-7 a phosphoethanolamine (PEA) substituent; and
(ii) an N. meningitidis LOS, in particular constituted by a non-detoxified lipid A, an inner core, an α chain of L6 type, in which the heptose II residue of the inner core bears in position O-3 a phosphoethanolamine (PEA) substituent and does not bear a PEA substituent in positions O-6 and O-7 or an LOS obtained according to preparation process (ii); or an N. meningitidis LOS in particular constituted by a lipid A, an inner core, an α chain of L6 type, in which the heptose II residue of the inner core bears in position O-3 and in position O-6 or O-7 a phosphoethanolamine (PEA) substituent; or obtained according to preparation process (i).

In the latter composition, the LOS of point (i) may advantageously be the LOS of the strain C708 lpt3FL lpt6TR lgtA.::erm or the LOS of the strain A1 (Zhu, Klutch & Tsai, FEMS Microbiology Letters (2001) 203: 173 and Gu, Tsai & Karpas, J. Clin. Microbiol. (August 1992) 30 (8): 2047).

Thus, a divalent vaccine composition i.a. according to the invention may be made up in various ways. The following 6 examples are mentioned:
1) A vaccine composition according to the invention, which comprises:
(i) an LOS obtained according to preparation process (i) or an N. meningitidis LOS in particular constituted by a lipid A, an inner core, an α chain of L6 type, in which the heptose II residue of the inner core bears in position O-3 and in position O-6 or O-7 a phosphoethanolamine (PEA) substituent; and
(ii) an LOS obtained according to preparation process (ii) or an N. meningitidis LOS in particular constituted by a lipid A, an inner core, an α chain of L6 type, in which the heptose II residue of the inner core bears in position O-3 a phosphoethanolamine (PEA) substituent and does not bear a PEA substituent in positions O-6 and O-7,
2) A vaccine composition according to the invention, which comprises:
(i) an LOS obtained according to preparation process (i) or an N. meningitidis LOS in particular constituted by a lipid A, an inner core, an α chain of L6 type, in which the heptose II residue of the inner core bears in position O-3 a phosphoethanolamine (PEA) substituent and does not bear a PEA substituent in positions O-6 and O-7; and
(ii) an N. meningitidis LOS in particular constituted by a lipid A, an inner core, an α chain of L6 type, in which the heptose II residue of the inner core bears in position O-6 or O-7 a phosphoethanolamine (PEA) substituent and does not bear a PEA substituent in position O-3,
3) A vaccine composition according to the invention which comprises:
(i) an LOS obtained according to preparation process (i) or an N. meningitidis LOS in particular constituted by a lipid A, an inner core, an α chain of L6 type, in which the heptose II residue of the inner core bears in position O-3 a phosphoethanolamine (PEA) substituent and does not bear a PEA substituent in positions O-6 and O-7; and
   (ii) an N. meningitidis LOS in particular constituted by a lipid A, an inner core, an α chain of L8 type, in which the heptose II residue of the inner core bears in position O-3 a phosphoethanolamine (PEA) substituent and does not bear a PEA substituent in positions O-6 and O-7,
4) A vaccine composition according to the invention which comprises:
   (i) an LOS obtained according to preparation process (i) or an N. meningitidis LOS in particular constituted by a lipid A, an inner core, an α chain of L6 type, in which the heptose II residue of the inner core bears in position O-3 and in position O-6 or O-7 a phosphoethanolamine (PEA) substituent; and
   (ii) an N. meningitidis LOS in particular constituted by a lipid A, an inner core, an α chain of L8 type, in which the heptose II residue of the inner core bears in position O-3 a phosphoethanolamine (PEA) substituent and does not bear a PEA substituent in positions O-6 and O-7,
5) A vaccine composition according to the invention, which comprises:
   (i) an LOS obtained according to preparation process (iii) or an N. meningitidis LOS in particular constituted by a lipid A, an inner core, an α chain of L8 type, in which the heptose II residue of the inner core bears in position O-3 and in position O-6 or O-7 a phosphoethanolamine (PEA) substituent; and
   (ii) an LOS obtained according to preparation process (ii) or an N. meningitidis LOS in particular constituted by a lipid A, an inner core, an α chain of L6 type, in which the heptose II residue of the inner core bears in position O-3 a phosphoethanolamine (PEA) substituent and does not bear a PEA substituent in positions O-6 and O-7,
6) A vaccine composition according to the invention, which comprises:
   (i) an LOS obtained according to preparation process (iii) or an N. meningitidis LOS in particular constituted by a lipid A, an inner core, an α chain of L8 type, in which the heptose II residue of the inner core bears in position O-3 and in position O-6 or O-7 a phosphoethanolamine (PEA) substituent; and
   (ii) an LOS obtained according to preparation process (ii) or an N. meningitidis LOS in particular constituted by a lipid A, an inner core, an α chain of L6 type, in which the heptose II residue of the inner core bears in position O-3 and in position O-6 or O-7 a phosphoethanolamine (PEA) substituent.

A vaccine/pharmaceutical composition according to the invention is especially useful for treating or preventing an infection caused by N. meningitidis, such as meningitis caused by N. meningitidis, meningococcemias and complications that may derive therefrom such as purpura fulminans and septic shock; and also arthritis and pericarditis caused by N. meningitidis.

It may be manufactured in a conventional manner. In particular, a therapeutically or prophylactically effective amount of the essential constituent of the vaccine, which is the LOS, is combined with a pharmaceutically acceptable support or diluent. Advantageously, it may also comprise a pharmaceutically acceptable adjuvant.

For use in a composition according to the invention, the LOS(s) (are) advantageously formulated as liposomes.

Additionally, a composition according to the invention may comprise one or more additional vaccine antigens of N. meningitidis; for example one or more N. meningitidis polypeptides. In a particularly preferred form, a composition according to the invention may comprise (i) the subunit B (TbpB) of the human transferrin receptor, which is an outer membrane lipoprotein of a certain number of non-enteric Gram-negative bacteria such as Neisseriae, e.g. N. meningitidis; or (ii) a lipidated N-terminal fragment thereof. In the latter case the lipidated TbpB or a lipidated fragment thereof may act both as a vaccine antigen and as an LOS adjuvant.

In N. meningitidis, the strains are divided into two isotypes: isotypes I and II, which differ according to the length of the TbpB amino acid chain (EP 560 969 and EP 586 266). With regard to isotype I, the reference strain is strain B16B6. With regard to isotype II, the reference strain is strain M982.

According to one advantageous embodiment, a composition according to the invention additionally comprises N. meningitidis isotype I or II lipidated TbpB or lipidated TbpB of each of isotype I and II strains. To this end, the lipidated TbpB of N. meningitidis isotype I strain may be that of strain B16B6; and the lipidated TbpB of N. meningitidis isotype II strain may be that of strain M982.

Therefore, it is cited as a matter of example:
1) A vaccine composition of the invention, which comprises:
   (i) a LOS obtained according to the preparation process (ii) or a N. meningitidis LOS in particular in particular constituted by a lipid A, an inner core, an α chain of L6 type, in which the heptose II residue of the inner core bears in position O-3 a phosphoethanolamine (PEA) substituent and does not bear a PEA substituent in positions O-6 and O-7; and
   (ii) the lipidated TbpB of a N. meningitidis strain of isotype II or a lipidated N-terminal fragment thereof.
2) A vaccine composition of the invention, which comprises:
   (i) a LOS obtained according to the preparation process (ii) or a N. meningitidis LOS in particular in particular constituted by a lipid A, an inner core, an α chain of L6 type, in which the heptose II residue of the inner core bears in position O-3 a phosphoethanolamine (PEA) substituent and does not bear a PEA substituent in positions O-6 and O-7; and
   (ii) the lipidated TbpB of a N. meningitidis strain of isotype II or a lipidated N-terminal fragment thereof; and
   (iii) the lipidated TbpB of a N. meningitidis strain of isotype I or a lipidated N-terminal fragment thereof.
3) A vaccine composition of the invention, which comprises:
   (i) a LOS obtained according to the preparation process (ii) or a N. meningitidis LOS in particular in particular constituted by a lipid A, an inner core, an α chain of L6 type, in which the heptose II residue of the inner core bears in position O-3 a phosphoethanolamine (PEA) substituent and does not bear a PEA substituent in positions O-6 and O-7; and
   (ii) a N. meningitidis LOS in particular in particular constituted by a lipid A, an inner core, an α chain of L8 type, in which the heptose II residue of the inner core bears in position O-3 a phosphoethanolamine (PEA) substituent and does not bear a PEA substituent in positions O-6 and O-7; or A LOS obtained according to the preparation process (iii); or a N. meningitidis LOS in particular in particular constituted by a lipid A, an inner core, an α chain of L8 type, in which the heptose II residue of the inner core bears in position O-3 and in position O-6 or O-7, a phosphoethanolamine (PEA) substituent; and (iii) the lipidated TbpB of a *N. meningitidis* strain of isotype II or a lipidated N-terminal fragment thereof; and optionally (iv) the lipidated TbpB of a *N. meningitidis* strain of isotype I or a lipidated N-terminal fragment thereof.

When a vaccine composition of the invention comprises one or more TbpB(s) this (these) latter can be formulated with the LOS in liposomes or be simply mixed with liposomes LOS (LOS formulated in liposomes).

The amounts of LOS per vaccine dose which are sufficient to achieve the abovementioned aims, and which are effective from an immunogenic, prophylactic or therapeutic point of view, depend on certain parameters that include the individual treated (adult, adolescent, child or infant), the route of administration and the administration frequency.

The amount of LOS per dose which is sufficient to achieve the abovementioned aims is in particular between 5 and 500 μg, advantageously between 10 and 200 μg, preferably between 20 and 100 μg, entirely preferably between 20 and 80 μg or between 20 and 60 μg, limits included.

The term "dose" employed above should be understood to denote a volume of vaccine administered to an individual in one go—i.e. at a time T. Conventional doses are of the order of a milliliter, for example 0.5, 1 or 1.5 ml; the definitive choice depending on certain parameters, and in particular on the age and the status of the recipient. An individual can receive a dose divided up into injections at several injection sites on the same day. The dose may be a single dose or, if necessary, the individual may also receive several doses a certain time apart—it being possible for this time apart to be determined by those skilled in the art.

It may be administered by any conventional route in use in the prior art, e.g. in the vaccines field, in particular enterally or parenterally. The administration may be carried out as a single dose or as repeated doses a certain time apart. The route of administration varies as a function of various parameters, for example of the individual treated (condition, age, etc.).

Finally, the invention also relates to:

a method for inducing in a mammal, for example a human, an immune response against *N. meningitidis*, according to which an immunogenically effective amount of a composition according to the invention is administered to the mammal so as to induce an immune response, in particular a protective immune response against *N. meningitidis*; and a method for prevention and/or treatment of an infection caused by *N. meningitidis*, according to which a prophylactically or therapeutically effective amount of a composition according to the invention is administered to an individual in need of such a treatment.

EXPERIMENTAL DATA

A Experimental Data Relating to the Strains Derived from *N. meningitidis* C708

1. Materials & methods 1.1 Transformation of Strain C708

Strain C708 is cultured in BHI (Brain Heart Infusion) agar medium at 37° C. under an atmosphere containing 10% $CO_2$. The bacterial lawn is harvested in BHI liquid medium complemented with 5 mM $MgCl_2$ to obtain a bacterial suspension at $10^9$ cfu/ml (cfu: colony-forming unit).

To 900 μl of the BHI liquid medium+5 mM $MgCl_2$ are added 10 μg of DNA necessary for the transformation (linearized plasmid); followed by 100 μl of the bacterial suspension ($10^8$ microorganisms). The transformation medium is incubated for 30 minutes at 37° C., 10% $CO_2$.

500 μl of this preparation (i.e. about $5.10^7$ cfu) serve to inoculate 4.5 ml of BHI+5 mM $MgCl_2$. The bacteria are left to regenerate for 2 hours at 37° C., 10% $CO_2$. Next, starting with this suspension, dilutions of BHI+5 mM $MgCl_2$ are made. 300 μl of a dilution containing about 30 000 cfu are plated out on a 140 mm agar BHI dish. The dishes are placed at 37° C., 10% $CO_2$ for at least 20 hours.

1.2. Blotting of the Transformant Colonies

The colonies are transferred onto 137 mm HYBOND-XL membrane (GE Healthcare; #RPN 137S). The microorganisms deposited on the membrane are lysed in denaturing buffer (0.5 M NaOH, 1.5 M NaCl). The membranes are washed with neutralizing buffer (0.5 M Tris, 1.5 M NaCl, pH 7.5); transferred into SSC 2× medium; and then dried. The DNA is bound by incubation for 2 hours at 80° C.

1.3. Detection of the Transformants by Hybridization with a Probe Labeled with $^{33}P$ dCTP Labeling of the probe is obtained by PCR amplification using the Ready-to-Go PCR Beads kit (GE Healthcare); the labeled probe is then purified on a PROBEQUANT G50 Microcolumn column (GE Healthcare).

The membranes to be hybridized are placed in threes in 50 ml of Rapid Hyb buffer (GE Healthcare) for 15 minutes at 65° C., with slow stirring, for prehybridization. The probe labeled and denatured beforehand for 2 minutes at 95° C. is added to the membranes. The final probe concentration is 5 ng/ml. Hybridization is allowed to continue for 2 hours at 65° C., with slow stirring.

The membranes are then subjected to successive washes by working as follows:

in low stringency buffer (2×SSC, 0.1% SDS (weight/vol)) 15 minutes at ambient temperature with slow stirring;

in medium stringency buffer (1×SSC, 0.1% SDS (weight/vol)) 20 minutes at 65° C. with slow stirring; and low stringency buffer (0.1×SSC, 0.1% SDS (weight/vol)) 45 minutes at 65° C. with slow stirring.

Once dried, the membranes are revealed by autoradiography (BIOMAX MR film).

1.4. Detection of the transformants by hybridization with an oligonucleotide labeled with [$\gamma^{32}$p] ATP Labeling of the 5' end of the oligonucleotide is performed in the following reaction medium (the amounts indicated are those corresponding to the hybridization of an amount of oligonucleotide necessary for the hybridization of 3 membranes in a dish):

| | | |
|---|---|---|
| free 5'-OH oligonucleotide | 3 μl max | i.e. 10 pmol |
| 10 X phosphorylation buffer | 1 μl | i.e. 1X |
| [$\gamma$-$^{32}$P] ATP 10 mCi/ml | 5 μl | i.e. 50 μCi |
| T4 kinase (10 U/μl) | 1 μl | i.e. 10 U |
| $H_2O$ | qs 10 μl | |

The reaction medium is incubated at 37° C. for 30 minutes. Next, the T4 kinase is inactivated by heating for 10 minutes at 70° C.

The membranes to be hybridized are placed in threes in 60 ml of Rapid Hyb buffer (GE Healthcare) for 15 minutes at 48° C., with slow stirring, for prehybridization. The prehybridization buffer is removed and replaced with 50 ml of hybridization buffer as follows: 5×SSC, 5×Denhardt's solution, 0.5% SDS (weight/vol.) and 100 µg/ml of salmon sperm DNA at 10 mg/ml sonicated and denatured for 5 minutes at 100° C.

The labeled oligonucleotide (10 µl) is added to the membranes. The hybridization is allowed to continue overnight at a temperature 5° C. below the Tm of the oligonucleotide, with gentle stirring.

The membranes are then subjected to successive washes by working in the order as follows:

in low stringency buffer (2×SSC, 0.1% SDS (weight/vol) 5 minutes at the Tm of the oligonucleotide −5° C., with slow stirring;

in medium stringency buffer (1×SSC, 0.1% SDS (weight/vol) 15 minutes at the Tm of the oligonucleotide −5° C., with slow stirring; and in low stringency buffer (0.1×SSC, 0.1% SDS (weight/vol) 10 minutes at the Tm of the oligonucleotide −5° C., with slow stirring.

Once dried, the membranes are revealed by autoradiography (BIOMAX MR film).

2. Construction of a Strain of *N. meningitidis* Expressing an LOS Having an α Chain is that of an LOS of Immunotype L6 and Comprising in Each of the Positions O3 and O6 of the Heptose II (Hep II) Residue of the Inner Core a Phosphoethanolamine (PEA) Substituent The starting strain used is *N. meningitidis* strain C708 of serogroup A and immunotype L6 having, inter alia, the following characteristics:

an active lgtA gene (gene switched "ON");

an lgtB gene—(non-functional gene);

an inactive lgtG gene (switched "OFF");

a truncated lpt3 gene;

an active lpt6 gene; and an active lot3 gene.

Strain C708 was filed on 11 Mar. 2008 at the Collection Nationale de Culture de Microorganisme, 25 rue du Dr Roux 75015 Paris, according to the terms of the treaty of Budapest. This strain bears the order number CNCM 1-3942.

Strain C708 comprises a truncated lpt3 gene. To modify it such that the LOS bears a PEA substituent in position 03, it is chosen to replace by homologous recombination the truncated lpt3 gene with the complete (full-length) lpt3 gene of the strain of *N. meningitidis* FAM18 serogroup C (strain made available worldwide to research laboratories). The strain resulting therefrom will be referred to for greater convenience as C708 lpt3 FL.

2.1. PCR (Polymerase Chain Reaction) Amplification of the Full-Length (FL) Lpt3 Gene of *N. meningitidis* Strain FAM18

100 ng of genomic DNA of the strain FAM18 were used for amplification with PLATINUM® Taq DNA polymerase High Fidelity (Invitrogen, #11304-011).

The pair of primers is as follows (pair No. 1):

```
                                    (SEQ ID NO: 8)
CG GAATTC GCC GTC TCA A ATG AAA AAA TCC CTT TTC

GTT CTC (Tm = 55.9° C.);
and (SEQ ID NO: 9)
AA CTGCAG TCA TTG CGG ATA AAC ATA TTC CG
(Tm = 57.1° C.);
```

(the EcoRI and PstI sites are respectively underlined).

The following mixture was used for amplification:

| Components | Volume | Final concentration |
|---|---|---|
| 10X High Fidelity PCR buffer | 5 μl | 1X |
| 10 mM dNTP mixture | 1 μl | 0.2 mM of each |
| 50 mM $MgSO_4$ | 2 μl | 2 mM |
| Mixture of primers (10 μM each) | 1 μl | 0.2 μM of each |
| Genomic DNA | x μl | 100 ng |
| PLATINUM ® Taq High Fidelity | 0.2 μl | 1.0 unit |
| Nuclease-free water | qs 50 μl final | Does not apply |

The thermocycler program is as follows:

| | | |
|---|---|---|
| Initial denaturing: | | 94° C. for 30 seconds |
| 30 cycles of: | denaturing: | 94° C. for 30 seconds |
| | hybridization: | 55° C. for 30 seconds |
| | extension: | 68° C. for 1 minute/kb of PCR product. |

After the reaction, 1/10 of the PCR product was deposited on agarose gel for verification.

2.2. Construction of a Transformation Vector

The PCR product, on the one hand, and the plasmid pUC19, on the other hand, were subjected to double digestion with EcoRI and PstI for 2 hours at 37° C. 10 units of each enzyme per g of DNA in REACT2 buffer (Invitrogen) were used.

The PCR fragment was then inserted into the linearized pUC19 vector. The ligations were performed in a final volume of 20 μl with 50 ng of vector, 0.5 U of T4 DNA ligase (Invitrogen) and 1 μl of 10 mM ATP (Invitrogen) for 16 hours at 16° C. The ligase was then inactivated by heating for 10 minutes at 65° C.

The vector thus obtained was transferred via the electroporation technique into a strain of *E. coli* XL1 blue MRF resistant to kanamycin and made electrocompetent. The parameters adopted for the electroporation are as follows: capacitance: 500 μFD; resistance: 200 ohms; voltage: 1700 volts.

Selection of the transformed clones was performed by plating out on 100 μg/ml ampicillin LB dishes. Authentification of 10 of the 50 positive clones was performed by PCR amplification. 100% of the clones had the expected profile. Finally, the $lpt^3$ gene in a plasmid of one of these clones (plasmid pM1222) was verified by sequencing.

2.3. Transformation of Strain C708 and Detection of the Homologous Recombination Event 2.3.1. Transformation 40 μg of pM1222 were digested with 400 U of EcoRI and 10 μg were used to transform the strain C708 according to the method described in section A.1.1.

After transformation, the bacteria were plated out onto 17 140 mm Petri dishes at a theoretical concentration of 30 000 cfu per dish; i.e. 510 000 cfu (colony-forming units) and were then placed overnight at 37° C. The dishes were then placed at +4° C. for 30 minutes.

After 24 hours at 37° C., counting of the control dishes made it possible to estimate the number of cfu as 27 000 per dish for the mutant.

2.3.2. Clone Selection

The recombination event, i.e. the replacement of the lpt3 TR (truncated) gene with the lpt3 FL (full-length) gene, was detected after transferring the clones onto hybridization membrane and hybridizing with a probe labeled with $^{33}P$ dCTP according to the methods described in sections A.1.2. and A.1.3.

Selection of the positive clones was made by hybridization of the DNA bound to the membranes with a DNA probe labeled with $^{33}$P dCTP corresponding to the truncated part of the lpt3 gene, which is thus present only in the recombinant clones.

Preparation of the Probe

In order to obtain the 270-bp lpt3 probe, 10 ng of the plasmid pUClpt3 were used for PCR amplification with PLATINUM® Taq DNA polymerase High Fidelity (Invitrogen, #11304-011).

The pair of primers is as follows (pair No. 2):

```
                                           (SEQ ID NO: 10)
CGC CGA ATA CTT TAT CTT GAG GC (Tm = 60.6° C.);
and (SEQ ID NO: 11)
CTC GCC AAA GAG CAG GGC (Tm = 60.5° C.).
```

For amplification, the following mixture was used:

| Components | Volume | Final concentration |
|---|---|---|
| 10X High Fidelity PCR buffer | 5 µl | 1X |
| 10 mM dNTP mixture | 1 µl | 0.2 mM of each |
| 50 mM MgSO$_4$ | 2 µl | 2 mM |
| Mixture of primers (10 µM each) | 1 µl | 0.2 µM of each |
| Plasmid pUC | x µl | 100 ng |
| PLATINUM ® Taq High Fidelity | 0.2 µl | 1.0 unit |
| Nuclease-free water | qs 50 µl final | Does not apply |

The thermocycler program is as follows:

| Initial denaturing: | | 94° C. for 30 seconds |
|---|---|---|
| 30 cycles of: | Denaturing: | 94° C. for 30 seconds |
| | Hybridization: | 55° C. for 30 seconds |
| | Extension: | 68° C. for 45 seconds. |

After the reaction, 1/10 of the PCR products was deposited on agarose gel to ensure the specificity of the amplicon, and the PCR fragment was then purified using the QIAQUICK PCR Purification Kit (Qiagen, #28104).

Hybridization and Revelation

The steps of labeling of the probe, hybridization, washing and revelation were performed as described in section A.1.3.

About 460 000 cfu were tested. After exposure with the BIOMAX MR films, the autoradiographs revealed 5 positive spots (C708 containing an lpt3 FL gene) each on a different membrane.

Screening and Authentification of the Positive Clones After locating on the Petri dish, part of the zone taken up around the positive clones was stored in freezing medium (M199 medium, 20% fetal calf serum, 10% glycerol) and the other part was used for the PCR Authentification.

To do this, each of the samples collected was first taken up in 80 µl of BHI broth, so as to plate out 30 µl of this suspension, as a mini-lawn on a BHI dish.

The remaining volume was centrifuged for 5 minutes at 6000 rpm and the pellet was then taken up in 50 µl of nuclease-free water. The microorganisms were lysed for 5 minutes at 95° C. and the supernatant, which serves as the matrix for the PCR reaction, was collected after centrifugation.

For each collected sample corresponding to a positive spot and for the controls, PCR amplification with the pair of primers that served for the 270 bp C708 lpt3 probe (pair No. 2) was performed with the EXPAND Long Template PCR kit (Roche) as described below.

| Components | Volume | Final concentration |
|---|---|---|
| 10X ELT PCR buffer | 5 µl | 1X |
| dNTP mixture (10 mM of each) | 2 µl | 0.4 mM of each |
| mixture of primers (10 µM of each) | 1.5 µl | 0.3 µM of each |
| DNA matrix | 40 µl | Does not apply |
| Polymerase ELT | 0.75 µl | 3.75 units |
| Nuclease-free water | qs 50 µl | Does not apply |

The thermocycler program is as follows:

| Initial denaturing: | | 94° C. for 2 min |
|---|---|---|
| 10 cycles of: | denaturing: | 94° C. for 10 seconds |
| | hybridization: | 54° C. for 30 seconds |
| | extension: | 68° C. for 45 seconds |
| 20 cycles of: | denaturing: | 94° C. for 15 seconds |
| | hybridization: | 54° C. for 30 seconds |
| | extension: | 68° C. for 45 seconds + 20 sec/cycle |
| Final elongation: | | 68° C. for 7 min |

After the reaction, 1/10 of the PCR products was deposited on agarose gel for verification. Four of the 5 clones had the expected profile. The frequency of production of a true positive clone was 1/115 000 cfu tested.

The following step consisted in isolating a pure clone. To do this, one of the heterogeneous positive clones was plated out as isolated cfus and several of these cfus (40) were analyzed by PCR, with the pairs of primers 1 or 2.

Each cfu was resuspended in 100 µl of nuclease-free water, 30 µl were deposited on a BHI dish and the remaining 70 µl were lysed for 5 minutes at 95° C., and the supernatant, which serves as the matrix for the PCR reaction, was collected after centrifugation.

The PCRs were performed with PLATINUM® Taq High Fidelity (Invitrogen) as already described for the amplification of the lpt3 probe. The hybridization temperature was 54° C.

After the reaction, 1/10 of the PCR products was deposited on agarose gel for verification. Five of the 40 clones proved to be pure clones.

The mini-lawn of pure clones was taken up in freezing medium, divided into 100 µl aliquots and stored at −70° C. The purity and the identity of this freezing material were validated.

3. Construction of a Strain of N. meningitidis Expressing an LOS Having an α Chain is that of an LOS of Immunotype L6 and Comprising Only in Position O3 of the Heptose II (Hep II) Residue of the Inner Core a Phosphoethanolamine (PEA) Substituent The starting strain used is N. meningitidis strain C708 lpt3 FL obtained as described previously. The objective is to inactivate the lpt6 gene of this strain by deletion of a central part of the gene.

3.1. PCR (Polymerase Chain Reaction) Amplification of the Full-Length Lpt6 Gene of N. meningitidis Strain Z2491 of Serogroup A (Gene NMA 0408)

100 ng of genomic DNA of strain Z2491 (strain made available worldwise to research laboratories) were used for amplification with PLATINUM® Taq DNA polymerase High Fidelity (Invitrogen, #11304-011).

The pair of primers is as follows (pair No. 3):

```
                                              (SEQ ID NO: 12)
CG GAATTC GCC GTC TCA A GGT TGC CTA TGT TTT CCT
GTT TTT G (Tm = 59.7° C.);
and
                                              (SEQ ID NO: 13)
AA CTGCAG CTA ACG GGC AAT TTT CAA AAC GTC
(Tm = 59.3° C.);
```

(the EcoRI and PstI sites are respectively underlined).

For amplification the following mixture was used:

| Components | Volume | Final concentration |
| --- | --- | --- |
| 10X High Fidelity PCR buffer | 5 µl | 1X |
| 10 mM dNTP mixture | 1 µl | 0.2 mM of each |
| 50 mM MgSO₄ | 2 µl | 2 mM |
| Mixture of primers (10 µM each) | 1 µl | 0.2 µM of each |
| Genomic DNA | x µl | 100 ng |
| PLATINUM ® Taq High Fidelity | 0.2 µl | 1.0 unit |
| Nuclease-free water | qs 50 µl final | Does not apply |

The thermocycler program is as follows:

| | | |
| --- | --- | --- |
| Initial denaturing: | | 94° C. for 30 seconds |
| 30 cycles of: | denaturing: | 94° C. for 30 seconds |
| | hybridization: | 55° C. for 30 seconds |
| | extension: | 68° C. for 1 minute/kb of PCR product. |

After the reaction, 1/10 of the PCR product was deposited on agarose gel for verification.

3.2. Construction of Vector pM1223 (pUC19 lpt6 FL)

The PCR product, on the one hand, and plasmid pUC19, on the other hand, were subjected to double digestion with EcoRI and PstI for 2 hours at 37° C. 10 units of each enzyme per g of DNA were used in the buffer REACT2 (Invitrogen).

The PCR fragment was then inserted into the linearized pUC19 vector. Ligations were performed on a final volume of 20 µl with 50 ng of vector, 0.5 U of T4 DNA ligase (Invitrogen) and 1 µl of 10 mM ATP (Invitrogen) for 16 hours at 16° C. The ligase was then inactivated by heating for 10 minutes at 65° C.

The vector thus obtained was transferred via the electroporation technique into a strain of E. coli XL1 blue MRF resistant to kanamycin and made electrocompetent. The parameters adopted for the electroporation are as follows: capacitance: 500 µFD; resistance: 200 ohms; voltage: 1700 volts.

Selection of the transformed clones was performed by plating out onto 100 µg/ml ampicillin LB dishes. Authentification of the positive clones (presence of an lpt6 FL gene) was performed by NdeI enzymatic digestion after extraction of the DNA by miniprep. Out of 20 clones analyzed, 6 had the expected profile. The recombinant plasmid of the selected clone was named pM1223.

3.3. Deletion of the Central Part of the Lpt⁶ Gene Originating from Strain Z2491

Construction of a Transformation Vector

With the EXPAND Long Template PCR kit (Roche), a reverse PCR was performed using the plasmid pM1223 with the aid of the following pair of primers (pair No. 4):

```
                                              (SEQ ID NO: 14)
CG GGATCC CAT CGA CAC GAA CGC CGC (Tm =
60.5° C.);
and
                                              (SEQ ID NO: 15)
CG GGATCC CCG CGC TTA ACG ACT ACA TC (Tm =
59.4° C.);
```

(the BamHI sites are underlined).

This makes it possible to amplify again the plasmid while deleting the part that it is desired to remove (808 bp).

The following mixture was used for amplification:

| Components | Volume | Final concentration |
| --- | --- | --- |
| 10X ELT PCR buffer | 5 µl | 1X |
| dNTP mixture (10 mM of each) | 2 µl | 0.4 mM of each |
| Mixture of primers (10 µM of each) | 1.5 µl | 0.3 µM of each |
| DNA matrix (pM1223) | 40 µl | Does not apply |
| Polymerase ELT | 0.75 µl | 3.75 units |
| Nuclease-free water | qs 50 µl | Does not apply |

The thermocycler program is as follows:

| | | |
| --- | --- | --- |
| Initial denaturing: | | 94° C. for 2 minutes |
| 10 cycles of: | denaturing: | 94° C. for 10 seconds |
| | hybridization: | 54° C. for 30 seconds |
| | extension: | 68° C. for 3 minutes |
| 20 cycles of: | denaturing: | 94° C. for 15 seconds |
| | hybridization: | 54° C. for 30 seconds |
| | extension: | 68° C. for 3 minutes + 20 sec/cycle |
| Final elongation: | | 68° C. for 7 minutes |

After the reaction, 1/10 of the PCR products was deposited on agarose gel.

After purification on a QIAQUICK column, the PCR product was digested with BamHI at a rate of 10 U of enzyme per µg of DNA. Once digested, it was purified by electroelution and then extracted with phenol-chloroform.

Self-ligation of the vector was performed in a final volume of 20 µl with 0.5 U of T4 DNA ligase (Invitrogen) and 1 µl of 10 mM ATP (Invitrogen) for 16 hours at 16° C. The ligase was then inactivated by heating for 10 minutes at 65° C.

The final step consisted in transferring the vector thus ligated into E. coli as described for pM1222. Authentification of the positive clones was performed by NdeI-PstI enzymatic digestion after extraction of the DNA by miniprep. Out of the 4 clones analyzed, 100% had the expected profile.

The recombinant plasmid of the selected positive clone was named pM1224, and this clone was stored in glycerol at −70° C. The presence in the plasmid pM1224 of an lgt6 gene with its central part deleted was confirmed by sequencing.

3.4. Transformation of Strain C708 Lpt3 FL and Detection of the Homologous Recombination Event Transformation 10 µg of plasmid pM1224 were linearized with EcoRI at a rate of 10 units of enzyme per µg of plasmid to be digested in the appropriate buffer for 2 hours at 37° C.

The transformation of strain C708 with plasmid pM1224 was performed according to the technique described in section A.1.1.

After transformation, the bacteria were plated out on 16 140 mm Petri dishes at a theoretical concentration of 50 000 cfu per dish; i.e. 800 000 cfu. The dishes were placed overnight at 37° C. and then placed for 30 minutes at +4° C.

Clone Selection: Preparation of the Probe, Hybridization and Revelation

The recombination event was detected after colony blotting and hybridization with an oligonucleotide labeled with γ$^{32}$P dATP.

The recombination event, i.e. the replacement of the lpt6 FL gene with the lpt6 TR gene, was detected after transferring the clones onto membrane and hybridization with a labeled probe according to the methods described in sections A.1.2. and A.1.4.

The clones transferred onto membranes were subjected to lysis and washing steps. The DNA is bound to the membranes by placing them for 2 hours at 80° C.

Selection of the positive clones was performed by hybridization of the DNA bound to HYBOND N+ membranes with a radioactive oligonucleotide whose sequence overlaps the two recombigenic ends. This is the following oligonucleotide: GTC GAT GGG ATC CCC GCG CTT AAC G (SEQ ID NO: 16) (Tm=69.5° C.).

About 840 000 cfu were tested. After exposure with BIOMAX MR films, the autoradiographs revealed 16 positive spots (C708 containing an lpt6 TR gene) divided among 9 different membranes.

Screening and Authentification of the Positive Clones

For each of the 16 positive spots, after detection on the Petri dish, part of the zone collected around the positive clones was stored in freezing medium (M199, 20% FCS, 10% glycerol) and the other part was used for the PCR Authentification.

To do this, the collected samples were first taken up in 80 µl of BHI broth, so as to plate out, as a mini-lawn on a BHI dish, 30 µl of each suspension.

The remaining volume was centrifuged for 5 minutes at 6000 rpm, and the pellet was then taken up in 50 µl of nuclease-free water. The microorganisms were lysed for 5 minutes at 95° C. and the supernatant, which serves as the PCR reaction matrix, was collected after centrifugation.

For each collected sample corresponding to a positive spot, a PCR amplification PCR was performed with the PLATINUM® Taq High Fidelity kit (Invitrogen) and the following pair of primers (pair No. 5)

```
                                              (SEQ ID NO: 17)
CCG ACT GGC GGA ATT GGG  (TM = 60.5° C.);
and (SEQ ID NO: 18)
CCC ATT TCT TCC TGA CGG AC  (Tm = 59.4° C.).
```

The following mixture was used for amplification:

| Components | Volume | Final concentration |
|---|---|---|
| 10X High Fidelity PCR buffer | 5 µl | 1X |
| 10 mM dNTP mixture | 1 µl | 0.2 mM of each |
| 50 mM MgSO$_4$ | 2 µl | 2 mM |
| Mixture of primers (10 µM each) | 1 µl | 0.2 µM of each |
| DNA matrix | x µl | 100 ng |
| PLATINUM ® Taq High Fidelity | 0.2 µl | 1.0 unit |
| Nuclease-free water | qs 50 µl final | Does not apply |

The thermocycler program is as follows:

| | | |
|---|---|---|
| Initial denaturing: | | 94° C. for 1 minute |
| 30 cycles of: | denaturing: | 94° C. for 30 seconds |
| | hybridization: | 55° C. for 30 seconds |
| | extension: | 68° C. for 50 seconds. |

After the reaction, 1/10 of the PCR product was deposited on agarose gel, for verification. Two candidates out of 16 proved to be true positives: i.e. a frequency of production of one true positive clone per 425 000 cfu tested.

The following step consisted in isolating a pure clone. To do this, one of the 2 heterogeneous positive clones was plated out as isolated cfus and several of these cfus (24) were analyzed by PCR, with the pair of primers No. 5.

Each cfu was resuspended in 50 µl of nuclease-free water, 20 µl were deposited on a BHI dish and the remaining 30 µl were lysed for 5 minutes at 95° C. and the supernatant, which serves as PCR reaction matrix, was collected after centrifugation.

The PCRs were performed with the PLATINUM® Taq High Fidelity kit (Invitrogen) as already described for the screening of the collected samples of the positive spots.

After the reaction, ⅕ of the PCR products was deposited on agarose gel for verification. Only one clone out of 24 proved to be a true positive.

The mini-lawn of the pure positive clone was taken up in freezing medium, divided into 100 µl aliquots and stored at −70° C. The purity and identity of this frozen material were confirmed.

4. Construction of a *N. meningitidis* Strain Expressing an LOS Having an α Chain which is that of an LOS of Immunotype L8 and Comprising a Single Phosphoethanolamine (PEA) Substituent in Position O3 of the Heptose II (Hep II) Residue of the Inner Core

*N. meningitidis* strain C708 lpt3 FL obtained as described previously in section A.3. is used as starting strain. The goal is to inactivate the lgtA gene of this strain by deletion of a central part of the gene.

4.1. PCR (Polymerase Chain Reaction) Amplification of the Full-Length lgtA Gene of *N. meningitidis* Strain MC58 of Serogroup B (Gene NMB 1929)

100 ng of genomic DNA of strain MC58 (strain made available worldwise to research laboratories) were used for amplification with PLATINUM® Taq DNA polymerase High Fidelity (Invitrogen, #11304-011).

The pair of primers is as follows:

```
                                              (SEQ ID NO: 19)
CG GAATTC GCC GTC TCA A ATG CCG TCT GAA GCC TTC

AG  (Tm = 59.4° C.);
and (SEQ ID NO: 20)
AA CTGCAG AAC GGT TTT TCA GCA ATC GGT  (Tm =
60.6° C.);
```

(the EcoRI and PstI sites are respectively underlined).

For amplification the following mixture was used:

| Components | Volume | Final concentration |
|---|---|---|
| 10X High Fidelity PCR buffer | 5 µl | 1X |
| 10 mM dNTP mixture | 1 µl | 0.2 mM of each |
| 50 mM MgSO$_4$ | 2 µl | 2 mM |
| Mixture of primers (10 µM each) | 1 µl | 0.2 µM of each |
| Genomic DNA | x µl | 100 ng |
| PLATINUM ® Taq High Fidelity | 0.2 µl | 1.0 unit |
| Nuclease-free water | qs 50 µl final | Does not apply |

The thermocycler program is as follows:

| | | |
|---|---|---|
| Initial denaturing: | | 94° C. for 30 seconds |
| 30 cycles of: | denaturing: | 94° C. for 30 seconds |
| | hybridization: | 55° C. for 30 seconds |
| | extension: | 68° C. for 1 minute/kb of PCR product. |

After the reaction, 1/10 of the PCR product was deposited on agarose gel for verification.

4.2. Construction of Vector pUC19 µgtA FL)

The PCR product obtained in A.4.1., on the one hand, and plasmid pUC19, on the other hand, were submitted to a double digestion with EcoRI and PstI for 2 hours at 37° C. 10 units of each enzyme per g of DNA were used in the buffer REACT2 (Invitrogen).

The PCR fragment was then inserted into the linearized pUC19 vector. Ligations were performed under a final volume of 20 µl with 50 ng of vector, 0.5 U of T4 DNA ligase (Invitrogen) and 1 µl of 10 mM ATP (Invitrogen) for 16 hours at 16° C. The ligase was then inactivated by heating for 10 minutes at 65° C.

The vector thus obtained was transferred by the electroporation technique into *E. coli* strain XL1 blue MRF kanamycin-resistant and made electrocompetent. The parameters adopted for the electroporation are as follows: capacitance: 500 FD; resistance: 200 ohms; voltage: 1700 volts.

Selection of the transformed clones was performed by plating out onto 100 µg/ml ampicilline LB dishes. Authentification of the positive clones (presence of an lgtA FL gene) was performed by NdeI enzymatic digestion after extraction of the DNA by miniprep. 1/5 of the analyzed clones had the expected profile.

4.3. PCR Amplification of the Erythromycine (Erm) Gene

PCR amplification of the erythromycine cassette (erm) was achieved using plasmid pMCG10 as template with primers allowing the introduction of restriction sites BamHI and XbaI.

The primer pair is as follows:

```
                                         (SEQ ID NO: 21)
CG GGATCC GGA AGG CCC GAG CGC AGA AGT (Tm:
65.7° C.);
and (SEQ ID NO: 22)
GC TCT AGA CAA CTT ACT TCT GAC AAC GAT CGG (Tm:
61° C.)
```

For amplification the following mixture was used:

| Components | Volume | Final concentration |
|---|---|---|
| 10X PFUTURBO buffer | 5 µl | 1X |
| 10 mM dNTP mixture | 0.4 µl | 0.2 mM of each |
| 50 mM MgSO$_4$ | 2 µl | 2 mM |
| Mixture of primers (10 µM each) | 1 µl | 0.2 µM of each |
| pMGC10 | x µl | 10 ng |
| PFUTURBO (Stratagene) | 0.2 µl | 2.5 units |
| Nuclease-free water | qs 50 µl final | Does not apply |

The thermocycler program is as follows:

| | | |
|---|---|---|
| Initial denaturing: | | 95° C. for 30 seconds |
| 30 cycles of: | denaturing: | 95° C. for 30 seconds |
| | hybridization: | 55° C. for 30 seconds |
| | extension: | 72° C. for 10 min. |

4.4. Construction of Plasmid pUC19 µgtA TR (Deletion of the Central Part of the lgtA Gene by Reverse PCR)

With the EXPAND Long Template PCR kit (Roche), a reverse PCR was achieved using plasmid pUC19 with the double objective of removing the central part of lgtA and of creating two restriction sites (BamHI and XbaI). The following pair of primers was used:

```
                                         (SEQ ID NO: 23)
CG GGATCC GCC AAT TCA TCC AGC CCG ATG (Tm =
61.8° C.);
and (SEQ ID NO: 24)
CG TCTAGA CCC GGT TCG ACA GCC TTG (Tm = 60.5° C.);
```

(the BamHI and XbaI sites are underlined).

This makes it possible to amplify AGAIN the plasmid while deleting the part that it is desired to remove.

The following mixture was used for amplification:

| Components | Volume | Final concentration |
|---|---|---|
| 10X ELT PCR buffer | 5 µl | 1X |
| dNTP mixture (10 mM of each) | 2 µl | 0.4 mM of each |
| Mixture of primers (10 µM of each) | 1.5 µl | 0.3 µM of each |
| 10 ng of pUC19 lgtA FL | | Does not apply |
| Polymerase ELT | 0.75 µl | 3.75 units |
| Nuclease-free water | qs 50 µl | Does not apply |

The thermocycler program is as follows:

| | | |
|---|---|---|
| Initial denaturing: | | 94° C. for 2 minutes |
| 10 cycles of: | denaturing: | 94° C. for 10 seconds |
| | hybridization: | 55° C. for 30 seconds |
| | extension: | 68° C. for 1 minute per kbs |
| 20 cycles of: | denaturing: | 94° C. for 15 seconds |
| | hybridization: | 55° C. for 30 seconds |
| | extension: | 68° C. for 1 minute per kbs + 20 sec/cycle |
| Final elongation: | | 68° C. for 7 minutes |

After the reaction, 1/10 of the PCR products was deposited on agarose gel for verifying the size (3.2 kbs). The PCR product was purified on a QIAQUICK column.

The final step has consisted in transferring the plasmid into *E. coli* strain XL1 blue MRF kanamycin-resistant and made electrocompetent as described above e.g. for pM1222.

Authentification of the positive clones (lgtA with a deleted central region) was performed by enzymatic digestion after extraction of the DNA by miniprep.

4.5. Construction of Plasmid pUC19 µgtA::erm

The PCR product erm, on the one hand, and the plasmid pUC19 µgtA TR obtained by reverse PCR, on the other hand, were submitted to a double digestion with BamHI and XbaI under the following conditions:

2 µg of DNA were mixed with 20 units of XbaI in 60 µL of buffer 2 (InVitrogen) for 2 hours 37° C. Then XbaI was inactivated by heating. 7 µL of NaCl 1 M, 20 BamHI units and 1 µL of buffer 2 were added. The reaction was performed for 2 hours at 37° C.

The digestion products were then deposited on a 0.8% agarose gel and after migration, bands were cut out for further electroelution (plasmid band migrates at 3.2. kbs).

Upon purification, the linearized plasmid and the digested PCR product erm were ligated together under ligation conditions as described previously. The ligation product has been used to transform as previously described, *E. coli* strain XL1 blue MRF kanamycin-resistant and made electro-competent. The recombinant clones were analyzed by enzymatic digestion. 4/11 of the analyzed clones had the expected digestion profile.

4.6. Transformation of Strain C708 Lpt3 FL Lpt6 TR and Detection of the Homologous Recombination Event 10 µg of plasmid pUC19 µgtA::erm were linearized with EcoRI at a rate of 10 units of enzyme per µg of plasmid to be digested in the appropriate buffer for 2 hours at 37° C.

The transformation of strain C708 was performed according to the technique described in section A.1.1.

After transformation, 1.24 $10^8$ bacteria were plated out on BHI+2 µg/mL erythromycine and incubated overnight at 37° C. The transformation rate was 1/2.5 $10^6$.

B. Experimental Data Relating to the Vaccine Compositions

1. Preparation of Lipidated rTbpB M982 and B16B6

In the interest of simplifying the language and reading, the term "rTbpB" or "TbpB" will subsequently be simply indicated.

1.1. Production

Strains expressing rTbpB M982 and B16B6

The expression strains are *E. coli* BL21 strains respectively containing plasmids TG9219 and TG9216. These plasmids contain in particular a kanamycin-selectable marker and the polynucleotide encoding the rTbpB from *N. meningitidis* strain M982 (pTG9219) or B16B6 (pTG9216) (the sequences of which are as described in patent EP 586 266) fused to the *E. coli* RlpB (real lipoprotein B) signal sequence and placed under the control of the arabinose promoter (araB).

Culture

Three frozen samples of *E. coli* BL21/pTG9219 or *E. coli* BL21/pTG9216 strain (each 1 ml) are used to inoculate 3 liters of LB (Luria Broth) medium divided up in Erlenmeyer flasks. The incubation is continued for 15 to 18 h at 37° C.

This preculture is used to inoculate a fermenter containing TGM16 medium (9 g/L yeast extract, 0.795 g/L $K_2SO_4$, 3.15 g/L $K_2HPO_4$, 0.75 g/L NaCl, 0.005 g/L $CaCl_2.2H_2O$, 0.021 g/L $FeCl_3.6H_2O$, 0.69 g/L $MgSO_4.7H_2O$, 37.5 g/L salt-free casein acid hydrolysate) supplemented with 20 g/L glycerol, in a proportion of 10% (vol./vol.).

The culturing is continued at 37° C. with shaking, at a pressure of 100 mbar and with an air feed of 1 L/min/L of culture, while readjusting, over time, the glycerol concentration to 20 g/L (e.g. at $OD_{600}$ of 15±_2). When the $OD_{600}$ is between 21 and 27, the rTbpB expression is induced by adding arabinose so as to obtain a final concentration of 10 g/L. After one hour of induction, the culture is stopped by cooling to around 10° C.

The bacterial pellets are recovered by centrifugation and stored in the cold.

1.2. Purification

Extraction of Membranes Containing the rTbpB

LOS Extraction

A bacterial pellet equivalent to one liter of culture (approximately 72 g of microorganisms, wet weight) is thawed at a temperature of 20° C.+/−5° C. The thawed (or partially thawed) microorganisms are resuspended with 800 ml of a solution, at ambient temperature, of 50 mM Tris HCl, 5 mM EDTA, pH 8.0. 9 protease inhibitor tablets (7 Complete Mini, EDTA free tablets; ROCHE ref. 11836170001+two Complete, EDTA free tablets; ROCHE ref. 11836170001) are immediately added. Since some of the microorganisms lyze spontaneously, 4 µl of benzonase (1 IU of DNAse activity/ml final concentration; Merck ref. K32475095) are also added. The incubation is continued at +4° C. for 45 minutes with magnetic stirring after homogenization with a TURRAX (15 sec.).

4 ml of 1M $MgCl_2$ are then added so as to be at a final concentration of 5 mM. The magnetic stirring is continued for 10 minutes. Centrifugation at 15 000 g for 45 minutes makes it possible to harvest the pellet (pellet P1; versus supernatant S1) containing the rTbpB protein.

A second extraction is carried out: homogenization with a TURRAX in 800 ml of the 50 mM Tris HCl buffer containing 5 mM EDTA, pH 8.0, and stirring for 30 min. $MgCl_2$ (8 ml of a molar solution) is added. The incubation is continued for 10 minutes. The suspension is centrifuged at 15 000 g for 1 hour 30.

Bacterial Lysis

The pellet is resuspended with 1400 ml of 50 mM Tris HCl supplemented with 4 protease inhibitor tablets with 8 µl of benzonase. The solution is homogenized with a TURRAX for 15 seconds. The lysis is carried out at +4° C. for 30 minutes through the addition of 14 ml (10 mg/ml final concentration) of lysozyme at 100 mg/ml in 25 mM Na acetate, 50% glycerol.

The suspension is centrifuged at 30 000 g for 30 minutes (pellet P2 containing the protein; versus supernatant S2 containing the contaminants of rTbpB). The pellet containing the membranes can be frozen at this stage.

Washing of Membrane Fragments

The lysis pellet P2 is taken up in 50 mM Tris HCl (1100 ml). After homogenization, (TURRAX 15 seconds), it is washed for one hour at +4° C. A centrifugation is carried out as previously at 30 000 g for 30 minutes. The pellet (P3; versus supernatant S3) is frozen at −45° C. 50 mM Tris HCl buffer makes it possible to remove a small amount of protein (supernatant S3) and solubilizes only very little rTbpB.

The pellet P3 is taken up in 50 mM Tris HCl buffer containing 8M urea, pH 8.0 (800 ml). This buffer makes it possible to remove a part of the contaminating proteins without solubilizing the membranes containing the rTbpB. After homogenization (without using a TURRAX), the solution is then stirred for one hour at +4° C. A centrifugation is carried out as previously at 30 000 g for 30 minutes, which makes it possible to obtain a membrane pellet which can be frozen.

Membrane Solubilization

The thawed membrane pellet is solubilized with 780 ml of 50 mM Tris HCl buffer containing 6 mM EDTA, 2M urea and 4% ELUGENT, at pH 7.5. The presence of the detergent at 4% and of the 2M urea makes it possible to solubilize the pellet. The solution is stirred at +4° C. overnight (minimum 16 h). Centrifugation of the solution at 30 000 g (1 hour at +4° C.) leaves only a small pellet (P4) containing a few impurities. The supernatant S4 containing the rTbpB protein is recovered for loading on a first cation exchange column (QS I).

Purification by Anion Exchange Chromatography on Q SEPHAROSE at pH 7.5

Two successive chromatographies are carried out. The product of the first chromatography is collected and then subsequently loaded, after a dialysis step, on a second chromatography column which uses different conditions (absence of EDTA).

1$^{st}$ Chromatography, in the Presence of EDTA (Chromatography QS I)

A column of 600 ml (K50, diameter 20 cm$^2$) of Q SEPHAROSE Fast Flow gel (ref. 17-0510-01 GE Healthcare) is mounted, tamped in equilibration buffer, 50 mM Tris HCl containing 6 mM EDTA, 2M urea and 1% ELUGENT, at pH 7.5, at the flow rate of 8 ml/minute.

The supernatant S4 (approximately 845 ml) is loaded at the flow rate of 6 ml/minute. The direct eluate (part which does not attach to the column during loading of the sample) contains the protein of interest, rTbpB. This eluate (1150 ml) is taken and then dialyzed at +4° C. (for 6 days) against 6 liters of 50 mM Tris HCl buffer containing 2 M urea and 1% ELUGENT, pH 7.5, in order to reduce the EDTA concentration to 1 mM and to remove NaCl.

2$^{nd}$ Chromatography (QS II), without EDTA

A K50 column of 490 ml of new Q SEPHAROSE Fast Flow gel is equilibrated in 50 mM Tris HCl buffer containing 2 M urea and 1% ELUGENT, pH 7.5.

The dialyzed solution (1080 ml) is loaded on the column (flow rate 6 ml/minute); then 5 saline elution steps in this same buffer are carried out: 20 mM, 50 mM, 100 mM, 250 mM and 1 M NaCl (working flow rate 6 ml/minute). The rTbpB protein is eluted from the column at two salt concentrations (50 mM and 100 mM). The 50 mM elution fraction is the fraction of interest, since the rTbpB protein therein is the purest and is present in a greater amount (2.6 times more protein than in the 100 mM NaCl fraction).

The pH of the fraction corresponding to the 50 mM NaCl elution peak is decreased, with magnetic stirring, to pH 5.5 by adding 1.7N acetic acid. The solution (860 ml) is dialyzed against 5 liters of 10 mM sodium acetate buffer containing 1M urea and 0.2% ELUGENT, pH 5.5 (24 hours at +4° C.) and then against 4 liters of 10 mM sodium acetate buffer containing 1M urea and 0.2% ELUGENT, pH 5.5 (17 hours at +4° C.).

Purification by Cation Exchange Chromatography on SP SEPHAROSE (SPI) at pH 5.5

A K50 column or 100 ml of new SP SEPHAROSE Fast Flow gel (Ge Healthcare, ref. 17-0729-01) is equilibrated in 10 mM sodium acetate buffer containing 1M urea and 0.2% ELUGENT, pH 5.5.

The dialyzed protein solution (850 ml) is loaded on the column (flow rate 6 ml/minute). Then, five saline elution steps are carried out: 50 mM, 100 mM, 250 mM, 500 mM and 1 M NaCl, in the buffer mentioned above.

The rTbpB protein is eluted exclusively in the 250 mM NaCl fraction and the low-molecular-weight contaminants are eliminated essentially in the direct eluate (40%). About 35 mg of purified rTbpB M982 are thus obtained and slightly less for rTbpB B16B6.

Dialysis and Concentration of the SPI Product (250 mM Fractions)

The fractions corresponding to the 250 mM elution peak of the SPI column are combined (volume 274 ml). The pH of the solution is brought back up to pH 7.3 by adding, with stirring, approximately 800 µl of 0.5N NaOH. The solution is dialyzed at +4° C. (Spectra Por 1: cutoff threshold 6-8000 D) against two 10 liter baths of PBS containing 0.2% ELUGENT, pH 7.1 (66 hours and 22 hours).

The dialysate is concentrated to a volume of 21.1 ml by frontal diafiltration concentration on a 30 kD AMICON membrane in PBS (ref. PBTK06510).

The concentrate obtained is then again dialyzed against 2 liters of PBS containing 0.2% ELUGENT, pH 7.1 (Slide A Lyser ref. 66810: cutoff threshold 10 kD).

The solution is then filtered aseptically through a 0.22 µm MILLEX filter with DURAPORE membrane (MILLIPORE ref. SLGV 033RS). The purified rTbpB protein batch obtained is frozen at −80° C. The protein concentration is 1642 µg/ml.

1.3. Preparation of rTbpB for Injection

The rTbpB solution obtained in section B.1.2. is treated by adsorption on BIO-BEADS™ SM-2 in order to remove the excess ELUGENT™ detergent (surfactant in particular constituted of alkyl glucosides) which could destabilize the LOS liposomes.

Activation of BIO-BEADS™

About 2.5 ml of methanol are added to 500 mg of BIO-BEADS™ and the mixture is homogenized intermittently for 15 min at ambient temperature. After a settling-out period, the supernatant is removed. This washing operation is repeated twice.

About 5 ml of ultra-filtered sterile water are then added and the mixture is homogenized intermittently for 15 min at ambient temperature. After a settling-out period, the supernatant is removed. This washing operation is repeated twice.

About 5 ml of PBS are then added and the mixture is homogenized intermittently for 15 min at ambient temperature. It is stored at 5° C. and used the same day.

At the end, the weight of the BIO-BEADS™ has increased by a factor R (equal to approximately 1.2).

Removal of the Detergent by Adsorption on BIO-BEADS™

The rTbpB solution obtained in section 1.2. contains 2 mg/ml of ELUGENT™. The amount of BIO-BEADS™ that has to be used is determined according to the amount of ELUGENT™ to be removed.

For one ml of the rTbpB solution obtained in section B.1.2., 29×R mg of activated BIO-BEADS™ are added. The mixture is vigorously stirred for one hour at ambient temperature. The maximum amount of liquid is then recovered and a final concentration of 0.001% of merthiolate is added thereto. The whole process is carried out under sterile conditions.

2. Preparation of the Purified LOS

Culture

Eight ml of frozen sample of any one of N. meningitidis C708 serogroup A strains described hereinabove or N. meningitidis strain A1 serogroup A that exclusively expresses immunotype L8 and exhibit a LOS bearing two PEAs, one in position 3, one in position 6 of heptose II, are used to inoculate 800 ml of Mueller-Hinton medium (Merck) supplemented with 4 ml of a solution of glucose at 500 g/l and divided up in Erlenmeyer flasks. The culture is continued with shaking at 36±1° C. for approximately 10 hours.

400 ml of a solution of glucose at 500 g/l and 800 ml of a solution of amino acids are added to the preculture. This preparation is used to inoculate a fermentor containing Mueller-Hinton medium, at an $OD_{600\ nm}$ close to 0.05. The fermentation is continued at 36° C., at pH 6.8, 100 rpm, $pO_2$ 30% under an initial airstream of 0.75 l/min/I of culture.

After approximately 7 hours ($OD_{600\ nm}$ of approximately 3), Mueller-Hinton medium is added at a rate of 440 g/h. When the glucose concentration is less than 5 g/l, the fermentation is stopped. The final $OD_{600\ nm}$ is commonly between 20 and 40. The cells are harvested by centrifugation and the pellets are frozen at −35° C.

Purification (method adapted by Westphal & Jann, (1965) Meth. Carbohydr. Chem. 5: 83)

The pellets are thawed and suspended with 3 volumes of 4.5% (vol./vol.) phenol with vigorous stirring for 4 hours at approximately 5° C. The LOS is extracted by phenol treatment.

The bacterial suspension is heated to 65° C. and then mixed vol./vol. with 90% phenol, with vigorous stirring for 50-70 min at 65° C. The suspension is subsequently cooled to ambient temperature and then centrifuged for 20 min at 11 000 g. The aqueous phase is removed and stored, while the phenolic phase and the interphase are harvested so as to be subjected to a second extraction.

The phenolic phase and the interphase are heated to 65° C. and then mixed with a volume of water equivalent to that of the aqueous phase previously removed, with vigorous stirring for 50-70 min at 65° C. The suspension is subsequently cooled to ambient temperature and then centrifuged for 20 min at 11 000 g. The aqueous phase is removed and stored, while the phenolic phase and the interphase are harvested so as to be subjected to a third extraction identical to the second.

The three aqueous phases are dialyzed separately, each against 40 l of water. The dialysates are then combined. One volume of 20 mM Tris, 2 mM $MgCl_2$ is added to 9 volumes of dialysate. The pH is adjusted to 8.0±0.2 with 4N sodium hydroxide.

Two hundred and fifty international units of DNAse are added per gram of pellet. The pH is adjusted to 6.8±0.2. The preparation is placed at 37° C. for approximately 2 hours with magnetic stirring, and then subjected to filtration through a 0.22 µm membrane. The filtrate is purified by passing it through a SEPHACRYL S-300 column (5.0×90 cm; PHARMACIA™).

The fractions containing the LOS are combined and the $MgCl_2$ concentration is increased to 0.5M by adding powdered $MgCl_2.6H_2O$, with stirring.

While continuing the stirring, dehydrated absolute alcohol is added to give a final concentration of 55% (vol./vol.). The stirring is continued overnight at 5±2° C., and then centrifugation is carried out at 5000 g for 30 min at 5±2° C. The pellets are resuspended with at least 100 ml of 0.5M $MgCl_2$ and then subjected to a second alcoholic precipitation identical to the preceding one. The pellets are resuspended with at least 100 ml of 0.5M $MgCl_2$.

The suspension is subjected to a gel filtration as previously described. The fractions containing the LOS are combined and filtration-sterilized (0.8-0.22 µm) and stored at 5±2° C.

This purification method makes it possible to obtain approximately 150 mg of LOS per liter of culture.

3. Preparation of [LOS] Liposomes by Detergent Dialysis
3.1. Preparation of Liposomes The LOS liposomes are prepared by detergent dialysis. Briefly, the lipids (EDOPC:DOPE) are made into the form of a lipid film and taken up in 10 mM Tris buffer, and then dispersed in the presence of 100 mM of octyl-β-D-glucopyranoside (OG) (Sigma-Aldrich ref. 08001) and filtered sterilely. The LOS in 100 mM OG is added sterilely. The lipids/LOS/OG mixture is then dialyzed against 10 mM Tris buffer in order to remove the OG and to form the liposomes.

Protocol

A lipid preparation in chloroform, of the lipids that will be used to produce the liposomes, is prepared. A dry film is obtained by complete evaporation of the chloroform.

A dry film of 1,2-dioleoyl-sn-glycero-3-ethylphosphocholine (EDOPC or ethyl-DOPC) and of 1,2-dioleoyl-sn-glycero-3-phosphoethanolamine (DOPE) in an EDOPC:DOPE mole ratio of 3 to 2 is obtained by mixing 12.633 ml of a solution of EDOPC (AVANTI Polar Lipids ref. 890704) at 20 mg/ml in chloroform and 7.367 ml of a solution of DOPE (AVANTI Polar Lipids ref. 850725) at 20 mg/ml in chloroform, and evaporating off the chloroform until it has completely disappeared.

The dry film is taken up with 30 ml of 10 mM Tris buffer, pH 7.0, so as to obtain a suspension containing 13.333 mg of lipids/ml (8.42 mg/ml of EDOPC and 4.91 mg/ml of DOPE). The suspension is stirred for 1 hour at ambient temperature and then sonicated for 5 min in a bath. 3.333 ml of a sterile 1M solution of octyl-β-D-glucopyranoside (OG) (Sigma-Aldrich ref. 08001) in 10 mM Tris buffer, pH 7.0, are then added, still with stirring, so as to obtain a clear suspension of lipids at 12 mg/ml, 100 mM OG and 10 mM Tris buffer. The stirring is continued for 1 h at ambient temperature on a platform shaker. Filtration is then carried out sterilely through a MILLEX HV 0.45 µm filter.

A composition is prepared, under sterile conditions, by bringing together LOS and lipids in a lipids:LOS mole ratio of 250 (0.160 mg/ml of LOS, 9.412 mg/ml of lipids and 100 mM of OG). 40 ml of such a composition are obtained from mixing the following preparations:

2.005 ml of 10 mM Tris buffer, pH 7.0; 0.223 ml of 100 mM OG in 10 mM Tris; 31.373 ml of the EDOPC:DOPE suspension having a mole ratio of 3:2, at 12 mg/ml in 100 mM OG, 10 mM Tris; and 6.4 ml of a sterile suspension of LOS at 1 mg/ml in 100 mM OG, 10 mM Tris.

After stirring for one hour at ambient temperature, the suspension is transferred sterilely into 4 sterile 10 ml dialysis cassettes. Each cassette is dialyzed 3 times (24 hrs-24 hrs-72 hrs) against 200 volumes of 10 mM Tris, pH 7.0, i.e. 2 l.

The liposomes are recovered under sterile conditions. The increase in volume after dialysis is approximately 30%.

Merthiolate and NaCl are added to this preparation so as to obtain a preparation of liposomes in 10 mM Tris, 150 mM NaCl, pH 7.0, 0.001% merthiolate, which ultimately contains approximately 110 µg/ml of LOS and 7 mg/ml of lipids, of which there are approximately 4.5 mg/ml of EDOPC and approximately 2.5 mg/ml of DOPE (theoretical concentrations).

The LOS liposomes are stored at +5° C.

3.2. Preparation of the Injectable Materials

The liposomes are adjusted to the required LOS concentration (in particular required for the immunogenicity tests) in 10 Mm Tris, 150 Mm NaCl, pH 7.4. The merthiolate concentration is maintained at 0.001%.

4. Preparation of an [LOS] Liposomes+rTbpB Mixture rTbpB in PBS (section B.1.3.) is mixed with [LOS] liposomes (section B.3.) in an rTbpB:LOS weight:weight ratio equal to 1. The volume is then adjusted with 10 mM Tris buffer containing 150 mM NaCl, pH 7.4, so as to obtain a preparation in which each of the components (rTbpB and LOS) is at a concentration of 80 µg/ml. The merthiolate concentration is maintained at 0.001%.

5. Production of an Endotoxoid (LOS Detoxified by Complexation with a Peptide Analog of Polymyxin B)

This endotoxoid is prepared as described in patent application WO 06/108586. Briefly, one volume of a solution of purified LOS at 1 mg/ml, sterilized by filtration through a 0.22 µm membrane, is mixed with one volume of a solution of SAEP2-L2 peptide at 1 mg/ml, sterilized by filtration through a 0.22 µm membrane.

The SAEP2-L2 peptide (SEQ ID NO: 3) is a peptide with an antiparallel dimeric structure, of formula:

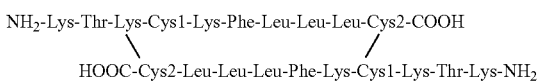

A precipitate forms immediately. Mixing is carried out for 5 min at ambient temperature, and then the mixture is left to stand overnight at 4° C. The precipitate is harvested by centrifugation at 3000 rpm for 10 min. The pellet is washed 5 times with one volume of pyrogen-free sterile water, pH 7.2. Finally, the pellet is resuspended in 10 mM Tris buffer containing 150 mM NaCl and TWEEN 80, pH 7.4, so as to obtain a suspension at 1 mg/ml, calculated based on the wet weight of the precipitate. The suspension is stored at 4° C.

6. Preparation of an Endotoxoid+rTbpB Mixture rTbpB in PBS (obtained as described in section B.1.3.) is mixed with endotoxoid (section B.5.) in a weight:weight ratio equal to 1. The volume is then adjusted with 10 mM Tris buffer containing 150 mM NaCl and 0.05% TWEEN 80 so as to obtain a preparation in which each of the components is at a concentration of 80 µg/ml.

7. Immunogenicity Study No. 1 in Rabbits

The various formulations tested were produced as described in one of the preceding sections.

7.1. Immunization of Rabbits

Twenty-four 7-week-old female NZ-KBL rabbits (Charles River Lab.) are divided up into 5 test groups of four and 2 control groups of two.

The female rabbits of each group receive, in a volume of 0.5 ml, divided up into 2 concomitant intramuscular injections in the legs, at D0, D21 and D42:

Group A: 40 µg of liposomes [LOS α chain L6, PEA-3]
   in 10 mM Tris, 150 mM NaCl, pH 7.4 buffer;
Group B: 40 µg of liposomes [LOS α chain L6, PEA-3] and 40 µg M982 rTbpB
   in 10 mM Tris, 150 mM NaCl, pH 7.4 buffer;
Group C: 40 µg of liposomes [LOS α chain L6, PEA-3, PEA-6]
   in 10 mM Tris, 150 mM NaCl, pH 7.4 buffer;
Group D: 40 µg of liposomes [LOS α chain L6, PEA-3, PEA-6] and 40 µg M982 rTbpB
   in 10 mM Tris, 150 mM NaCl, pH 7.4 buffer;
Group E: 40 µg of LOS α chain L6, PEA-3 in endotoxoid form and 40 µg M982 rTbpB
   in 10 mM Tris, 150 mM NaCl, 0.5% TWEEN, pH 7.0 buffer;
Group F (control): 40 µg rTbpB and empty liposomes
   in 10 mM Tris, 150 mM NaCl, pH 7.4 buffer; and
Group G (control): empty liposomes in 10 mM Tris, 150 mM NaCl, pH 7.4 buffer.

A blood sample is taken from the animals for analysis at D0, D42 (before the third injection) and at D56.

7.2. Assaying of Anti-LOS Antibodies by ELISA

This assay is automated (Staccato automation system, Caliper) according to the following protocol:

The wells of DYNEX™ 96-well plates are impregnated with, for each of the groups, 1 µg of LOS homolog in 1×PBS (phosphate buffered saline) buffer, pH 7.1, 10 mM $MgCl_2$, and the plates are incubated for 2 hours at 37° C. and then overnight at 4° C. The plates are blocked by adding, to the wells, 150 µl of PBS containing 0.05% of TWEEN 20 and 1% (weight/vol) of skimmed milk powder (PBS-TWEEN-milk). The plates are incubated for 1 hour at 37° C.

Serial doubling dilutions of the test samples are prepared in PBS—0.05% TWEEN—1% milk. The plates are incubated for 90 min at 37° C. and then washed 3 times with PBS+TWEEN 20 at 0.05%.

A peroxidase-anti-mouse IgG or peroxidase-anti-rabbit IgG conjugate in PBS-TWEEN-milk is added to the wells and the plates are incubated for 90 min at 37° C. The plates are washed three times. 100 µl of a ready-to-use solution of TMB (3,3',5,5'-tetramethylbenzidine, substrate for peroxidase) are distributed per well. The plates are incubated in the dark for 20 min at ambient temperature. The reaction is stopped by adding 100 µl of 1M HCl per well.

The optical density is measured at 450-650 nm with an automatic reader (Multiskan Ascent). In the absence of standard, the antibody titers are determined as being the reciprocal dilution giving an optical density of 1.0 on a tendency curve (CodUnit software). The antibody detection threshold is 1.3 $log_{10}$ ELISA unit. For each titer below this threshold, an arbitrary value of 1.3 $log_{10}$ is assigned.

7.3. Measurement of the Bactericidal Activity of IgGs Purified Against N. meningitidis Strains Heterologous to the Strain C708 (SBA Test)

IgGs were purified from pooled sera by affinity chromatography using HiTrap rProtein A FF column (GE Healthcare/Amersham Biosciences) according to the supplier's recommendations.

On the basis of the purified IgGs, serial twofold dilutions are carried out in gelatin-containing Dulbecco's PBS with calcium and magnesium ions. The dilutions are carried out in a 96-well plate for a final volume of 50 µl per well.

The bactericidal activity of the purified IgGs has been tested against the strains mentioned in the table which follows:

Twenty-five µl of a culture of N. meningitidis in the exponential phase ($4 \times 10^3$ CFU/ml) in BHI medium in the absence of an agent which chelates iron in free form (so as to avoid expressing TbpB), and also 25 µl of baby rabbit complement at 1/1.5, are added to each well. The plate is incubated for one hour at 37° C., with shaking.

Fifty µl of the mixture of each well are then deposited on bioMerieux Mueller-Hinton agar plates and incubated overnight at 37° C. under 10% $CO_2$. The number of clones is counted.

There are three controls:
bacteria+baby rabbit complement, without test serum ("complement" control);
bacteria+inactivated baby rabbit complement, without test serum ("microorganism" control); and
bacteria+inactivated baby rabbit complement+test serum (serum control).

The bactericidal titer is expressed as the inverse of the dilution giving 50% bacterial death by comparison with the "complement" control.

7.4. Results and Discussion

ELISAs

Figure 3:
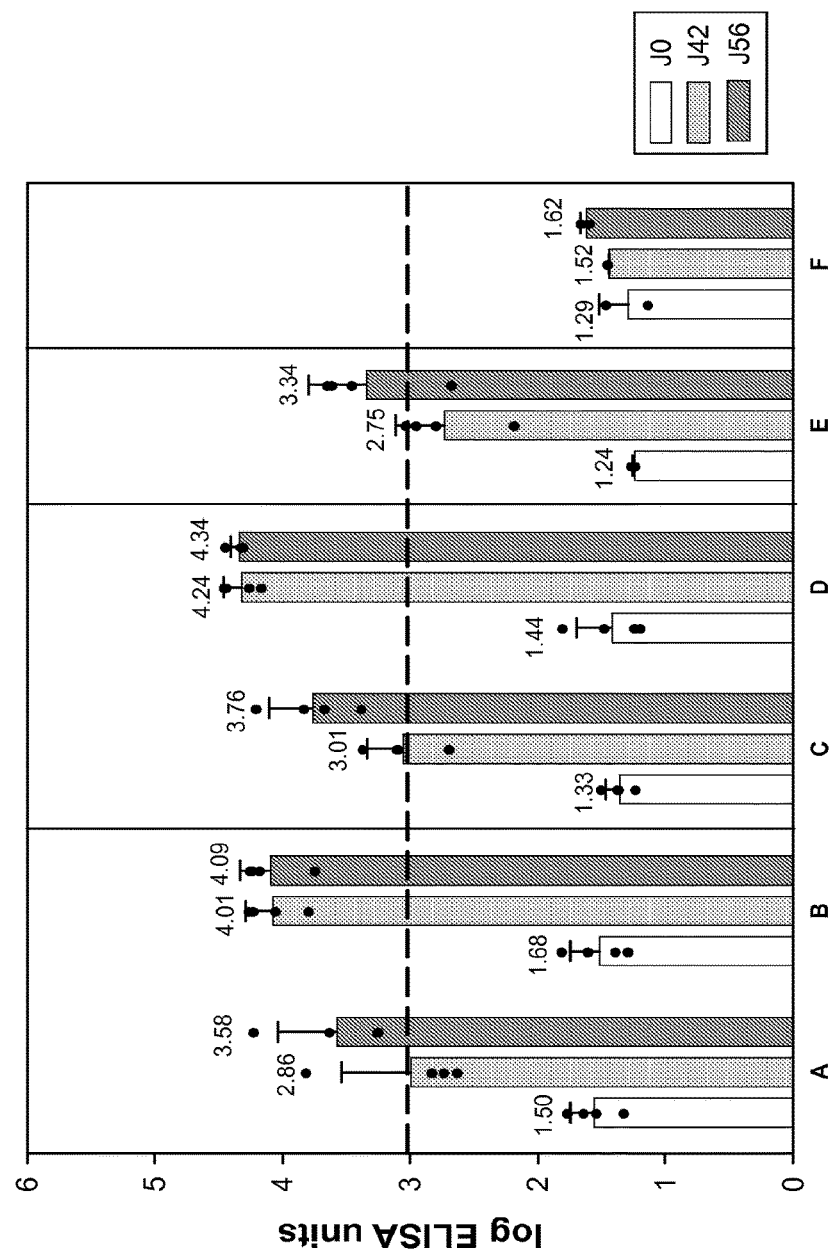
FIG. 3 shows the ELISA titers expressed as $\log_{10}$ of the anti-LOS IgGs of the rabbit sera of groups A, B, C, D, E and F in the Immunogenicity study No. 1 in rabbits.

FIG. 3 gives the ELISA titers expressed as $log_{10}$ of the anti-LOS IgGs of the rabbit sera of groups A, B, C, D, E and F. In white, the titers of the sera before immunization; shaded, those of the sera of which samples were taken at D42 after the second immunization; and darkly shaded, those of the sera of which samples were taken at D56.

The ELISA titers at times D42 and D56 show that the LOS obtained from each of the strains C708 constructed as described previously is immunogenic. This immunogenicity is increased by the presence of lipidated rTbpB for each period under consideration (which confirms the adjuvant power of this lipoprotein).

SBA Test

The bactericidal activity has been established in "fold increase" as being the purified IgG bactericidal titer of a considered group: negative control group titer ratio. As such, the seroconversion rate in "fold increase" expresses the bactericidal titer increase. It is considered that the bactericidal activity is significant when a "fold increase" equal or above ×8 is obtained.

Purified IgGs from control group G exhibit against all tested strains a «fold increase» inferior to ×4.

The «fold increase» values obtained with purified IgGs from groups B and D against 18 strains are reported in table IV hereinafter:

TABLE IV

Strains included in the cross SBA study cultured in the absence of chelating agent

| IT | TbpB Isotype | Epidémio-logical complex | Name | LOS in liposomes: L6 PEA-3 + Lipidated TbpB M982 | L6 PEA-3, -6 + Lipidated TbpB M982 |
|---|---|---|---|---|---|
| L3 | II | ST-32 | BZ83 | < × 4 | < × 4 |
| | II | ST-41/44 | LNP23015 | ×8 | ×8 |
| | II | ST-41/44 | LNP22979 | < × 4 | < ×4 |
| | II | ST-41/44 | BZ138 | ×8 | ×4 |
| | II | ST-41/44 | 95/46 | ×8 | ×4 |
| | II | | S3032 | < × 4 | < × 4 |
| | II | | LNP22763 | < × 4 | < × 4 |
| | II | | M982 | ×256 | ×168 |
| | II | | NG144/82 | ×16 | ×16 |
| | II | | NGF26 | < × 4 | < × 4 |
| L4-like | II | ST-8 | BZ163 | ×8 | ×4 |
| | | ST-8 | NGH41 | ×8 | < × 4 |
| L8 | II | | 8680 | < × 4 | < × 4 |
| | II | ST-41/44 | RH873 | < × 4 | < × 4 |
| L1 | II | ST-41/44 | 92/123 | < × 4 | < × 4 |
| | I | ST-269 | No28 LO 05-2606 | ×4 | <× 4 |
| | II | ST-269 | No 60 AA 07-1734 | ×16 | ×16 |
| N.d. | II | | EG327 | < × 4 | < × 4 |

*: LOS in liposomes + adjuvant (lipidated rTbpB)

Purified IgGs obtained after immunisation with the group B composition (40 µg liposomes [LOS chaîne α L6, PEA-3] and 40 µg rTbpB M982) have then been tested against a larger number of strains. The results are reported in tables V and VI hereinafter.

8. Immunogenicity Study No. 2 in Rabbits

The various test formulations were manufactured as described in one of the preceding sections.

8.1. Immunization of Rabbits

Twenty-four 7-week-old NZ KBL female rabbits (Charles River Lab.) are dispatched into 4 test groups of four (groups A to D) and 4 groups of 2 (groups E and H).

The female rabbits of each group receive in a volume of 0.5 ml divided among 2 concomitant intramuscular injections into the legs, on D0, D21 and D42:

Group A: 40 µg of liposomes [LOS α chain L8, PEA-3, PEA-6] et 40 g rTbpB M982,
  in 10 mM Tris, 150 mM NaCl, pH 7.4 buffer;
Group B: 40 g of liposomes [LOS α chain L8, PEA-3, PEA-6] and 40 µg rTbpB B16B6,
  in 10 mM Tris, 150 mM NaCl, pH 7.4 buffer;
Group C: 40 µg of liposomes [LOS α chain L8, PEA-3] and 40 µg rTbpB M982,
  in 10 mM Tris, 150 mM NaCl, pH 7.4 buffer;
Group D: 40 µg of liposomes [LOS α chain L8, PEA-3, PEA-6]
  in 10 mM Tris, 150 mM NaCl, pH 7.4 buffer;
Group E: 40 µg rTbpB M982 and 40 µg of LOS-free liposomes
  in 10 mM Tris, 150 mM NaCl, 0.5% TWEEN, pH 7.0 buffer;
Group F: 40 µg rTbpB B16B6 and 40 µg of LOS-free liposomes
  in 10 mM Tris, 150 mM NaCl, 0.5% TWEEN, pH 7.0 buffer;
Group G: 40 µg of liposomes [LOS α chain L8, PEA-3]
  in 10 mM Tris, 150 mM NaCl, pH 7.4 buffer;
Group H: 10 mM Tris, 150 mM NaCl, pH 7.4 buffer Blood is collected from the animals for analysis at D0, D42 (before the third injection) and at D56.

8.2. Measurement of the Bactericidal Activity of Purified IgGs Against Strains of N. meningitidis Heterologous to the Strain C708

IgGs were purified from pooled sera by affinity chromatography using the HiTrap rProtein A FF column (GE Healthcare/Amersham Biosciences) according to the manufacturer's recommendations.

Using the purified IgGs, twofold serial dilutions are performed in Dulbecco's gelatinized PBS containing calcium and magnesium ions. The dilutions are performed in a 96-well plate for a final volume of 50 µl per well.

The bactericidal activity of the purified IgGs was tested against the strains mentioned in Table V below:

25 µl of an N. meningitidis culture in the exponential phase ($4 \times 10^3$ CFU/ml) in BHI medium+50 M of DESFERAL (agent for chelating iron in free form, to allow the expression of TbpB) and 25 µl of baby rabbit complement at 1/1.5 are added to each well. The plate is incubated for one hour at 37° C. with stirring.

50 µl of the mixture in each well are then deposited on bioMerieux Mueller-Hinton agar dishes and incubated overnight at 37° C. under 10% $CO_2$. The number of clones is counted.

There are three controls:

bacteria+baby rabbit complement, without test serum ("complement" control);

bacteria+inactivated baby rabbit complement, without test serum ("microorganism" control); and bacteria+inactivated baby rabbit complement+test serum (serum control).

The bactericidal titer is expressed as being the inverse of the dilution giving 50% bacterial death by comparison with the "complement" control.

8.3. Results and Discussion

SBA Test

34 N. meningitidis strains have been tested for cross bactericidal activity. Their names are to be seen in table V hereinafter. The results are expressed in «fold increase» according to the calculation methodology described in section B.7.4. hereinabove.

As expected, purified IgGs from negative control immunisation group do not show any bactericidal activity against any of the strains.

Purified IgGs from immunisation groups D and G (LOS not adjuvanted with TbpB) exhibit a bactericidal activity of less interest. For simplicity' sake, table V hereinafter only shows the SBA results expressed in «fold increase», obtained with purified IgGs from groups A, B, C, E and F of the second study together with the results obtained with the purified IgGs of group B of the first study.

Table VI shows the SBA results expressed in «fold increase», of purified IgGs from immunisation group B of the first study and of group A of the second study against 22 strains cultured in presence/absence of DESFERAL.

Table VII shows for a variety of vaccine compositions, the percentage of protection deduced from the cross SBA studies including 34 strains cultured in presence of DESFERAL.

TABLE V

| | | | LOS in liposomes: | | | | | |
|---|---|---|---|---|---|---|---|---|
| 34 strains included in the cross SBA study, cultured in the presence of DESFERAL | | | L6 PEA-3 + Lipidated TbpB M982 Study | L8 PEA-3, -6 + Lipidated TbpB M982 Study | L8 PEA-3 + Lipidated TbpB M982 Study | L8 PEA-3, -6 + Lipidated TbpB B16B6 Study | Empty liposomes + Lipidated TbpB M982 Study | Empty liposomes + Lipidated TbpB B16B6 Study |
| IT | TbpB Isotype | Name | n° 1 Group B | n° 2 Group A | n° 2 Group C | n° 2 Group B | n° 2 Group E | n° 2 Group F |
| | | | (i) | | | | | |
| L3 | II | BZ83 | x32 | x32 | x16 | <x4 | x16 | <x4 |
| | II | LNP23015 | x16 | x16 | x16 | <x4 | x16 | <x4 |
| | II | LNP20443 | <x4 | ≤x4 | <x4 | <x4 | <x4 | <x4 |
| | II | LNP22979 | x8 | x32 | x8 | <x4 | <x4 | <x4 |
| | II | BZ138 | x512 | x256 | x256 | <x4 | x256 | <x4 |
| | II | 95/46 | x64 | x16 | x8 | <x4 | x64 | <x4 |
| | II | S3032 | x4 | x4 | x4 | <x4 | <x4 | <x4 |
| | II | LNP22763 | x4 | x4 | <x4 | <x4 | <x4 | <x4 |
| | II | M982 | >x1024 | x512 | x512 | <x4 | x256 | <x4 |
| | II | NG144/82 | x64 | x138 | x64 | <x4 | x128 | <x4 |
| | II | H44/76 | x8 | x4 | x4 | <x4 | <x4 | <x4 |
| | II | MC58 | x32 | x8 | x4 | <x4 | x16 | <x4 |
| | II | NGPB24 | x8 | x4 | x8 | <x4 | x16 | <x4 |
| | II | NGF26 | x4 | x4 | <x4 | <x4 | <x4 | <x4 |
| | | | (ii) | | | | | |
| L4-like | II | BZ163 | x16 | x16 | x8 | x4 | <x4 | <x4 |
| | I | NGP20 | <x4 | <x4 | <x4 | x1024 | <x4 | x1024 |
| | I | M986 | <x4 | <x4 | <x4 | x1024 | <x4 | x512 |
| L4 | II | M2 | x16 | <x4 | <x4 | <x4 | <x4 | <x4 |
| L8 | II | 8680 | x4 | x256 | x256 | x16 | <x4 | <x4 |
| | II | RH873 | x16 | x256 | x256 | x64 | x8 | <x4 |
| L1 | II | 92/123 | x8 | x32 | x32 | x16 | x4 | <x4 |
| | II | M101/93 | x16 | x16 | x16 | <x4 | x4 | <x4 |
| | II | 1000 | <x4 | x4 | x4 | x8 | <x4 | <x4 |
| | I | N° 28 LO 05-2606 | x16 | x8 | x16 | x128 | x8 | x16 |
| | II | N° 60 AA 07-1734 | x256 | x128 | x256 | x64 | x32 | <x4 |
| L2 | II | BZ157 | x8 | <x4 | <x4 | <x4 | <x4 | <x4 |
| | II | BZ232 | x16 | x32 | x16 | <x4 | x16 | <x4 |
| | I | B16B6 | <x4 | <x4 | <x4 | x1024 | <x4 | x512 |
| | | | (iii) | | | | | |
| N.d. | II | 30 | x128 | x128 | x64 | <x4 | x16 | <x4 |
| | II | 62 | x4 | x8 | x4 | <x4 | <x 4 | <x4 |
| | I | FAM18 | <x4 | <x4 | <x4 | x1024 | <x4 | x512 |
| | II | 90/94 | x16 | <x4 | x4 | <x4 | x4 | <x4 |
| | II | 22 | <x4 | x16 | x32 | x16 | <x4 | <x4 |
| | II | EG327 | <x4 | <x4 | <x4 | <x4 | <x4 | <x4 |

In Table V hereinabove:
IT means « immunotype »
L6 means a LOS bearing an α chain of type L6
L8 means a LOS bearing an α chain of type L8
PEA-3 means that the LOS bears a unique PEA substituent in position 3 of heptose II
PEA-3, -6 means that the LOS bears a PEA substituent in position 3 and a PEA substituent in position 6 of heptose II

TABLE VI

| | | | | L6 PEA-3 + Lipidated TbpB M982 Study n° 1 Group B | | L8 PEA-3, -6 + Lipidated TbpB M982 Study n° 2 Group A | |
|---|---|---|---|---|---|---|---|
| | | LOS in liposomes: Strains included in the cross SBA study, cultured in presence (DESFERAL)/ absence of chelating | | | | | | |
| IT | TbpB Isotype | Epidemiological complex | Name | Without chelating agent | With chelating agent | Without chelating agent | With chelating agent |
| L3 | II | ST-32 | BZ83 | <x4 | x32 | <x4 | x32 |
| | II | ST-41/44 | LNP23015 | x8 | x16 | <x4 | x16 |

TABLE VI-continued

| | | LOS in liposomes: Strains included in the cross SBA study, cultured in presence (DESFERAL)/ absence of chelating | | L6 PEA-3 + Lipidated TbpB M982 Study n° 1 Group B | | L8 PEA-3, -6 + Lipidated TbpB M982 Study n° 2 Group A | |
|---|---|---|---|---|---|---|---|
| IT | TbpB Isotype | Epidemio- logical complex | Name | Without chelating agent | With chelating agent | Without chelating agent | With chelating agent |
| | II | ST-41/44 | LNP22979 | <x4 | x 8 | <x4 | x32 |
| | II | ST-41/44 | BZ138 | x8 | x512 | x32 | x256 |
| | II | ST-41/44 | 95/46 | x8 | x64 | <x4 | x16 |
| | II | | S3032 | <x4 | x4 | <x4 | x4 |
| | II | | LNP22763 | <x4 | x4 | <x4 | x4 |
| | II | | M982 | x256 | >x1024 | x64 | x512 |
| | II | | NG144/82 | x16 | x64 | x4 | x128 |
| | II | | H44/76 | <x4 | x8 | <x4 | x4 |
| | II | | NGF26 | <x4 | x4 | <x4 | x4 |
| | II | | 62 | <x4 | x4 | <x4 | x8 |
| L4- like | II | ST-8 | BZ163 | x8 | x8 | x8 | x16 |
| L8 | II | | 8680 | <x4 | x4 | x128 | x256 |
| | II | ST-41/44 | RH873 | <x4 | x16 | x64 | x256 |
| L1 | II | ST-41/44 | 92/123 | <x4 | x8 | x16 | x32 |
| | I | ST-269 | N° 28 LO 05-2606 | x4 | x16 | <x4 | x8 |
| | II | ST-269 | N° 60 AA 07-1734 | x16 | x256 | x64 | x128 |
| N.d. | II | | EG327 | <x4 | <x4 | <x4 | <x4 |
| L2 | II | | BZ157 | <x4 | x8 | <x4 | <x4 |
| | II | | BZ232 | <x4 | x16 | <x4 | x32 |
| | I | | B16B6 | <x4 | <x4 | <x4 | <x4 |

TABLE VII

| Vaccine composition | % of protection deduced from cross SBA studies including 34 strains cultured in the presence of Desferal |
|---|---|
| L6 PEA O3 + TbpB M982 | 61.8% |
| L8 PEA O3, O6 + TbpB M982 | 55.9% |
| L6 PEA O3 + L8 PEA O3, O6 + TbpB M982 | 70.6% |
| L8 PEA O3 + TbpB M982 | 52.9% |
| L6 PEA O3 + L8 PEA O3 + TbpB M982 | 67.6% |
| L8 PEA O3, O6 + TbpB B16B6 | 32% |
| L6 PEA O3 + TbpB M982 + TbpB B16B6 | 73.5% |
| L8 PEA O3, O6 + TbpB M982 + TbpB B16B6 | 58.8-67.6% |
| L6 PEA O3 + L8 PEA O3, O6 + TbpB M982 + TbpB B16B6 | 82.4% |
| L8 PEA O3 + TbpB M982 + TbpB B16B6 | 64.7% |

The invention claimed is:

1. A process for preparing a lipooligosaccharide (LOS) of *Neisseria meningitidis*, the process comprising (a) culturing a modified a modified *N. meningitidis* strain exhibiting a lipooligosaccharide (LOS) comprising a lipid A, an inner core, and an L8 type alpha chain in which the heptose II residue of the inner core bears in position 0-3 and in position 0-6 or position 0-7 a phosphoethanolamine (PEA) substituent, wherein the modified *N. meningitidis* strain is made by a process comprising modifying an *N. meningitidis* strain of immunotype L8 so that it expresses an *N. meningitidis* lpt6 gene; and (b) harvesting the LOS from the culture of (a);

wherein the LOS comprises a lipid A, an inner core, and an alpha chain of L8 immunotype, and wherein the heptose II residue of the inner core bears in position 0-3 and in position 0-6 or position 0-7 a phosphoethanolamine (PEA) substituent.

2. A process for preparing a lipooligosaccharide (LOS) of *Neisseria meningitidis*, the process comprising (a) culturing a modified a modified *N. meningitidis* strain exhibiting a lipooligosaccharide (LOS) comprising a lipid A, an inner core, and an L8 type alpha chain in which the heptose II residue of the inner core bears in position 0-3 and in position 0-6 or position 0-7 a phosphoethanolamine (PEA) substituent, wherein the modified *N. meningitidis* strain is made by a process comprising modifying a serogroup A *N. meningitidis* strain of immunotype L8 so that it expresses an *N. meningitidis* lpt6 gene; and (b) harvesting the LOS from the culture of (a);

wherein the LOS comprises a lipid A, an inner core, and an a chain of L8 immunotype, and wherein the heptose II residue of the inner core bears in position 0-3 and in position 0-6 or position 0-7 a phosphoethanolamine (PEA) substituent.

3. The process according to claim 1 wherein the LOS is harvested in a form combined with outer membrane vesicles (OMVs).

4. The process according to claim 1 wherein the LOS is extracted for further purification.

5. The process according to claim 2 wherein the LOS is harvested in a form combined with outer membrane vesicles (OMVs).

6. The process according to claim 2 wherein the LOS is extracted for further purification.

7. A lipooligosaccharide (LOS) of *N. meningitidis* prepared by the process of claim 1.

8. A lipooligosaccharide (LOS) of *N. meningitidis* prepared by the process of claim 2.

9. A lipooligosaccharide (LOS) of *N. meningitidis* prepared by the process of claim 3.

10. A lipooligosaccharide (LOS) of *N. meningitidis* prepared by the process of claim 4.

11. A lipooligosaccharide (LOS) of *N. meningitidis* prepared by the process of claim 5.

12. A lipooligosaccharide (LOS) of *N. meningitidis* prepared by the process of claim 6.

* * * * *